US008993740B2

(12) United States Patent
Bajza et al.

(10) Patent No.: US 8,993,740 B2
(45) Date of Patent: Mar. 31, 2015

(54) METHOD FOR PREPARATION OF THE TETRASACCHARIDE LACTO-N-NEOTETRAOSE (LNNT) CONTAINING N-ACETYLLACTOSAMINE

(75) Inventors: István Bajza, Debrecen (HU); Gyula Dekany, Sinnamon Park (AU); Károly Ágoston, Telki (HU); Ignacio Figuero-Pérez, Miami, FL (US); Julien Boutet, La Plaine sur Mer (FR); Markus Hederos, Svedala (SE); Ferenc Horváth, Pilisszentkereszt (HU); Piroska Kovács-Pénzes, Jászberény (HU); Lars Kröger, Hamburg (DE); Christoph Röhrig, Mühlingen (DE); Andreas Schroven, Barssel (DE); Ioannis Vrasidas, Salonika (GR); Péter Trinka, Budapest (HU); László Kalmár, Váncsod (HU); Irme Kovács, Debrecen (HU); Sándor Demkó, Debrecen (HU); Ágnes Ágoston, Telki (HU); Christian Risinger, Rottweil (DE)

(73) Assignee: Glycom A/S, Kongens Lyngby (DK)

(*) Notice: Subject to any disclaimer, the term of this patent is extended or adjusted under 35 U.S.C. 154(b) by 0 days.

(21) Appl. No.: 13/579,741

(22) PCT Filed: Feb. 21, 2011

(86) PCT No.: PCT/DK2011/050053
§ 371 (c)(1),
(2), (4) Date: Aug. 17, 2012

(87) PCT Pub. No.: WO2011/100980
PCT Pub. Date: Aug. 25, 2011

(65) Prior Publication Data
US 2012/0309949 A1  Dec. 6, 2012

(30) Foreign Application Priority Data
Feb. 19, 2010  (DK) .................................. 2010 70060

(51) Int. Cl.
| | |
|---|---|
| *C07H 15/04* | (2006.01) |
| *C07H 15/14* | (2006.01) |
| *C07H 15/203* | (2006.01) |
| *C07H 17/02* | (2006.01) |
| *C07H 13/04* | (2006.01) |
| *A61K 31/715* | (2006.01) |
| *A61K 31/7016* | (2006.01) |
| *C08B 37/00* | (2006.01) |
| *C07H 15/18* | (2006.01) |
| *A23L 1/09* | (2006.01) |
| *A23L 1/30* | (2006.01) |
| *C07H 11/00* | (2006.01) |

(52) U.S. Cl.
CPC . *C07H 15/18* (2013.01); *A23L 1/09* (2013.01);
*A23L 1/30* (2013.01); *C07H 11/00* (2013.01);
*C07H 13/04* (2013.01); *A23V 2002/00* (2013.01)
USPC .......... 536/17.5; 536/53; 536/17.2; 536/18.4; 536/4.1; 514/54; 514/53; 514/25; 514/24

(58) Field of Classification Search
USPC ............ 536/17.5, 53, 17.2, 18.4, 4.1; 514/54, 514/53, 25, 24
See application file for complete search history.

(56) References Cited

FOREIGN PATENT DOCUMENTS

| | | |
|---|---|---|
| EP | 0870841 A1 | 10/1998 |
| EP | 1405856 A1 | 4/2004 |
| JP | 10-234394 | 9/1998 |

OTHER PUBLICATIONS

Yan et al. (Carbohydrate Research (2000), 328(1), 3-16).*
Greene et al. (Greene's Protective Groups in Organic Synthesis, Wiley 2007, p. 138).*
Braga, D., et al. Chem. Asian J. (vol. 6, pp. 2214-2223) 2011.*
Ivanisevic, I., et al. Pharm Form. & Quality Aug./Sep. 2011, pp. 30-33.*
Ponpipom et al., "Synthesis of Paragloboside Analogs", Tetrahedron Letters No. 20, pp. 1717-1720, 1978, Pergamon Press Ltd.
Yan et al., "Polymer-supported and Chemoenzymatic Synthesis of the *Neisseria meningitidis* Pentasaccharide: a Methodological Comparison", Carbohydrate Research 328; pp. 3-16, 2000; Elsevier Science Ltd.
Broeder et al., "Glycosyl Azides as Building Blocks in Convergent Syntheses of Oligomeric Lactosamine and Lewisx Saccharides", Bioorganic & Medicinal Chemistry, 1997, vol. 5, No. 1; pp. 1-19.
Bommer et al., "Synthesis of Lactoneotetrasyl Ceramide", Glycosyl imidiates, 43. Liebigs Ann. Chem. 1989; pp. 1107-1111.
Aly et al., "Synthesis of Lacto-N-Neotetraose and Lacto-N-Tetraose Using the Dimethylmaleoyl Group as Amino Protective Group", Carbohydrate Research 316; Elsevier Science Ltd., 1999; pp. 121-132.

(Continued)

*Primary Examiner* — Shaojia Anna Jiang
*Assistant Examiner* — Michael C Henry
(74) *Attorney, Agent, or Firm* — McHale & Slavin, P.A.

(57) ABSTRACT

The present invention relates to a method for preparation of the tetrasaccharide lacto-N-neotetraose (LNnt, formula (I)) especially in large scale, as well as intermediates in the synthesis, a new crystal form (polymorph) of LNnt, and the use thereof in pharmaceutical or nutritional compositions.

(I)

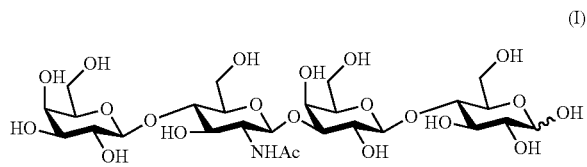

14 Claims, 3 Drawing Sheets

(56) References Cited

OTHER PUBLICATIONS

Sherman et al., "Study of Glycosylation with N-trichloroacetyl-D-glucosamine Derivatives in the Syntheses of the Spacer-armed Pentasaccharides Sialyl lacto-N-neotetraose and sialyl lacto-N-tetraose, their Fragments, and Analogues". Carbohydrate Research 336; pp. 13-46, 2001. Elsevier Science Ltd.

Yamada et al., "Syntheses of a Series of lacto-N-neotetraose Clusters Using a Carbosilane Dendrimer Scaffold", Carbohydrate Research 341; pp. 467-473, 2006; Elsevier Ltd.

Malleron et al., "Chemo-enzymatic Suppported Synthesis of the 3-sulfated Lewisa Pentasaccharide on a Multimeric Polyetylene Glycol", Carbohydrate Research 343; pp. 970-976, 2008.

Paulsen et al., "Regioselektive glycosylerung an stellungen 3' und 4' von lactose-derivaten", CarbohydrateResearch , 169; pp. 105-125, 1987.

Maranduba et al., "Glycosylation of Lactose. Synthesis of Methyl O-(2-acetamido-2-deoxy-β-D-glucopyranosyl)-(1→3)-O-β-D-galactopyranosyl-(1→4)-β-D-glucopyranoside and methyl O-β-D-galactopyranosyl-(1→4)-O-(2-acetamido-2-deoxy-β-D-glucopyranosyl)-(1→3)-O-β-D-galactopyranosyl-(1→4)-β-D-glucopyranoside". Carbohydrate Research, 135; pp. 330-336, 1985.

Dahmén et al., "Synthesis of di-, tri, and tetra-saccharides Corresponding to Receptor Structures Recognised by *Streptococcus pneumoniae*"; Carbohydrate Research, 138, pp. 17-28; 1985.

Maranduba et al., "Glycosylation of lactose: Synthesis of Branched Oligosaccharides involved in the Biosynthesis of Glycolipids Having Blood-group I Activity", Carbohydrate Research, 151; pp. 105-119, 1986.

Akira Kobata, "Isolation of Oligosaccharides from Human Milk", Methods Enzymol 1972; 28:262-271.

Sabesan et al., "Combined Chemical and Enzymatic Synthesis of Sialyloligosachharides and Characterization by 500-MHz 1H and 13C NMR Spectroscopy", J. Am. Chem. Soc. 1986; 108:2068-2080.

Murata et al., "Facile Enzymatic Conversion of Lactose into Lacto-N-Tetraoese and Lacto-N-Neotetraose", Glycoconjugate Journal 16; pp. 189-195, 1999.

Blixt et al. "Enzymatic Glycosylation of Reducing Oligosaccharides Linked to a Solid Phase or a Lipid via a Cleavable Squarate Linker", Carbohydrate Research 319; Elsevier Science Ltd., 1999; 319, pp. 80-91.

Renaudie et al., "Enzymatic Supported Synthesis of Lacto-N-Neotetraose Using Dendrimeric Polyethylene Glycol", Carbohydrate Research 339; pp. 693-698, 2004.

Zurabyan et al., "Synthesis of tri- and Tetrasaccharides Forming Structural Isomers of the Oligosaccharides Milk", Soviet J. Bioorg. Chem. 1978; 4:679-685; Plenum Publishing Corporation, 1979.

Kochetkov et al., "Synthesis of the Capsular Polysaccharide of *Streptococcus pneumoniae* Type 14", Tetrahedron 1987, vol. 43, No. 13; pp. 3109-3121.

Lemieux et al., "Syntheses of Derivatives of N-aceyl-D-lactosamine from D-lactal Hexaacetate, Hexa-O-acetyl-2-deoxy-2-phthalimido-β-D-lactosyl Chloride". Can. J. Chem. 1982; 60:63-67.

Sato et al., "Total Synthesis of a Stage Specific Embryonic Antigen-1 (SSEA-1) Glycoheptaosyl Ceramide V3FuncLc6Cer1", Tetrahedron Letters, vol. 29, No. 37; pp. 4759-4762, 1988; Pergamon Press plc.

Broeder et al., "A New Method of Anomeric Protection and Activation Based on the Conversion of Glycosol Azides into Glycosyl Fluorides", Carbohydrate Research, 249; Elsevier Science Publishers 1993; pp. 221-241.

Paulsen et al., "Synthese der tetra- und trisaccharid-sequenzen von asialo-GM1 und -GM2 lenkung der regioselectivitat der glycosidierung von lactose", Carbohydrate Research, 137; pp. 39-62, 1985.

Lubineau et al., "Chemoenzymatic Synthesis of a 3IV, 6III-disulfated Lewisx Pentasaccharide, a Candidate Ligand for Human L-selectin", Carbohydrate Research 305; pp. 501-509; 1998.

Database REGISTRY, RN 13007-32-4, STN entry date Nov. 16, 1984.

Kuhn, Richard, et al., "Über drei saure Pentasaccharide aus Frauenmilch," Chem. Ber., 1962, vol. 95, p. 513.

Kuhn, Richard, et al., "Die Konstitution der Lacto-N-neotetraose," Chem Ber, 1962, vol. 95, p. 518-519.

\* cited by examiner

METHOD FOR PREPARATION OF THE TETRASACCHARIDE LACTO-N-NEOTETRAOSE (LNNT) CONTAINING N-ACETYLLACTOSAMINE

CROSS-REFERENCE TO RELATED APPLICATIONS

This application is a §371 national stage entry of International Application No. PCT/DK0211/050053, filed Feb. 21, 2011, which claims priority to DK Patent Application No. 2010 70060 filed Feb. 19, 2010, the entire contents of which are incorporated herein by reference.

FIELD OF THE INVENTION

The present invention relates to a method for the preparation of Galpβ1-4GlcNAcpβ1-3Galpβ1-4Glc (LNnT), especially in large scale, as well as to intermediates and a new crystal form (polymorph) of LNnT.

BACKGROUND OF THE INVENTION

During the past decades the interest for preparation and commercialisation of human milk oligosaccharides (HMOs) has been increasing steadily. The importance of HMOs is directly linked to their unique biological activities such as antibacterial, antiviral, immune system and cognitive development enhancing activities.

The tetrasaccharide Galpβ1-4GlcNAcpβ1-3Galpβ1-4Glc (lacto-N-neotetraose, LNnT, Scheme 1) is one of the oligosaccharides occurring in human milk [Kuhn et al. *Chem. Ber.* 1962, 95, 513 and 518, Kobata *Methods Enzymol.* 1972, 28, 262]. LNnT act as bacterial receptor for pneumococci and it was found to be useful in the recognition of the acceptor specificity of glycosyltransferases, the substrate specificity of glycosidases and the structure of antigenic determinants. Furthermore LNnT represents a core structural element of more complex oligosaccharides, in glycolipids and in glycoproteins (paragloboside, 6-sialyl-LNnT, etc.) with various physiological activities.

Scheme 1. Lacto-N-neotetraose, LNnT

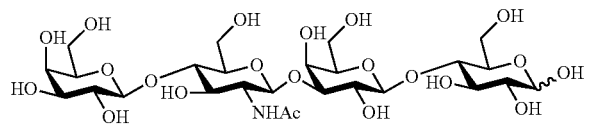

To date, access to large volumes of LNnT has not been possible by using isolation, biotechnology and synthetic methodologies. The isolation of LNnT from human milk is rather difficult even in milligram quantities due to the presence of a large number of similar oligosaccharides.

Enzymatic synthesis of LNnT consists of incubation of lacto-N-triose II with UDP-galactose in the presence of a galactosyltransferase [Sabesan et al. *J. Am. Chem. Soc.* 1986, 108, 2068; EP-A-870841] or with lactose in the presence of β-D-galactosidase [Murata et al. *Glycoconj.* 1999, 16, 189; JP 10-234394 A]. Enzymatic galactosylation of the proper trisaccharide bound to solid support was also elaborated [Blixt et al. *Carbohydr. Res.* 1999, 319, 80; Renaudie et al. ibid. 2004, 339, 693]. These complex enzymatic systems represent very expensive methodologies and difficult purification protocols for scale-up productions of LNnT.

Total synthetic procedures towards LNnT published [Zurabyan et al. Soviet *J. Bioorg. Chem.* 1978, 4, 679; Paulsen et al. *Carbohydr. Chem.* 1987, 169, 105; Aly et al. ibid. 1999, 316, 121] comprise plenty of reaction steps, protecting group manipulations and chromatographic purification, poor yields, and provide only milligram quantity of LNnT, thus they do not offer attractive techniques for large scale preparation. Synthesis of 1-O-benzyl-LNnT as benzyl analogue of paragloboside has also been published [Ponpipom et al. *Tetrahedron Lett.* 1978, 20, 1717].

When isolated from natural source [Kuhn et al. *Chem. Ber.* 1962, 95, 513] or made by enzymatic way [EP-A-1405856] LNnT was characterized as a crystalline material.

With respect of LNnT and intermediates towards it there is still a need for crystalline products which may simplify isolation, purification and formulation problems so far envisaged.

SUMMARY OF THE INVENTION

The first aspect of the present invention relates a method for the preparation of Galpl-4GlcNAcpβ1-3Galpβ1-4Glc (LNnT) comprising the steps of:

a) reaction of a donor characterized by general formula 5

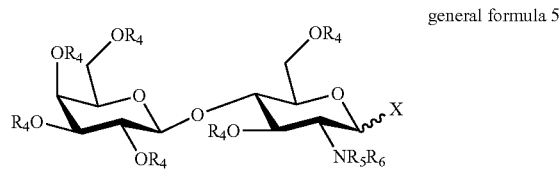

general formula 5 wherein $R_4$ is optionally substituted acyl,

—$NR_5R_6$ is selected from —$NAc_2$, —NH-haloacyl, phthalimide, tetrachlorophthalimide, 2,3-diphenylmaleimide and 2,3-dimethylmaleimide, X is selected from halogen, —OC(=NH)CCl$_3$, —OAc, —OBz and —SR$_7$, wherein R$_7$ is selected from alkyl and optionally substituted phenyl, with an acceptor of general formula 6

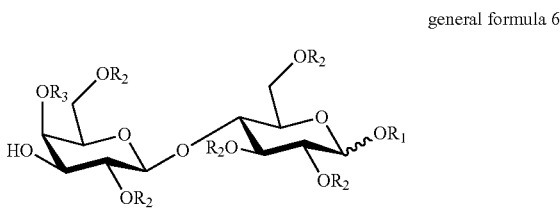

general formula 6 wherein $R_1$ is a group removable by catalytic hydrogenolysis, $R_2$ is optionally substituted acyl and $R_3$ is selected from optionally substituted acyl or H, to yield a compound of general formula 4

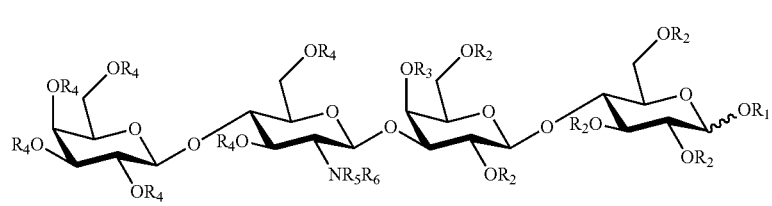

general formula 4 wherein $R_1$, $R_2$, $R_3$, $R_4$ and $-NR_5R_6$ are as defined above, b) converting the compound of general formula 4 into a compound of general formula 1

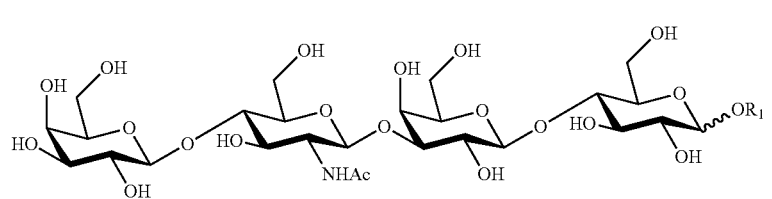

general formula 1 wherein $R_1$ is as defined above, c) crystallizing the compound of general formula 1, and d) subsequently subjecting the compound of general formula 1 to catalytic reduction.

The second aspect of the present invention provides a polymorph of Galpβ1-4GlcNAcpβ1-3Galpβ1-4Glc (LNnT).

The third aspect of the present invention relates to the polymorph of Galpβ1-4GlcNAcpβ1-3Galpβ1-4Glc (LNnT) for use as pharmaceutical agent.

The fourth aspect of the present invention provides the polymorph of Galpβ1-4GlcNAcpβ1-3Galpβ1-4Glc (LNnT) for use as nutritional additive.

The fifth aspect of the present invention relates to a pharmaceutical composition comprising the polymorph of Galpβ1-4GlcNAcpβ1-3Galpβ1-4Glc.

The sixth aspect of the present invention provides a nutritional composition comprising the polymorph of Galpβ1-4GlcNAcpβ1-3Galpβ1-4Glc.

The seventh aspect of the present invention relates to a compound of general formula 1'

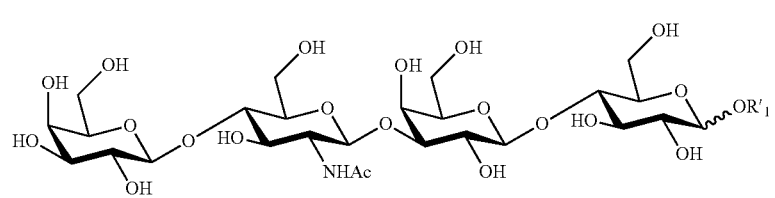

general formula 1' wherein $R'_1$ is selected from substituted benzyl, optionally substituted benzhydryl, optionally substituted trityl and optionally substituted naphthylmethyl.

The eighth aspect of the present invention provides a compound of general formula 2'

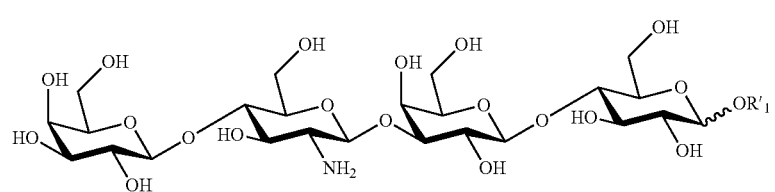

general formula 2' wherein $R'_1$ is selected from substituted benzyl, optionally substituted benzhydryl, optionally substituted trityl and optionally substituted naphthylmethyl.

The ninth aspect of the present invention relates to a compound of general formula 3

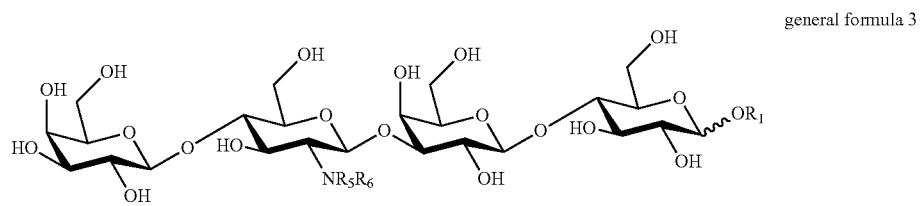

general formula 3 wherein $R_1$ is selected from optionally substituted benzyl, optionally substituted benzhydryl, optionally substituted trityl and optionally substituted naphthylmethyl, and —$NR_5R_6$ is selected from —NH-haloacyl, phthalimide, tetrachlorophthalimide, 2,3-diphenylmaleimide and 2,3-dimethylmaleimide.

The tenth aspect of the present invention provides a compound of general formula 4'

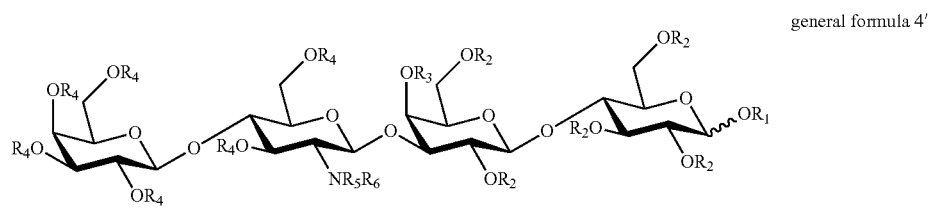

general formula 4' wherein $R_1$ is selected from optionally substituted benzyl, optionally substituted benzhydryl, optionally substituted trityl and optionally substituted naphthylmethyl, and each of $R_2$ and $R_4$ are independently optionally substituted acyl, $R_3$ is selected from optionally substituted acyl and H, —$NR_5R_6$ is selected from —$NAc_2$, —NH-haloacyl, tetrachlorophthalimide, 2,3-diphenylmaleimide and 2,3-dimethylmaleimide.

The eleventh aspect of the present invention relates to a compound of general formula 4a

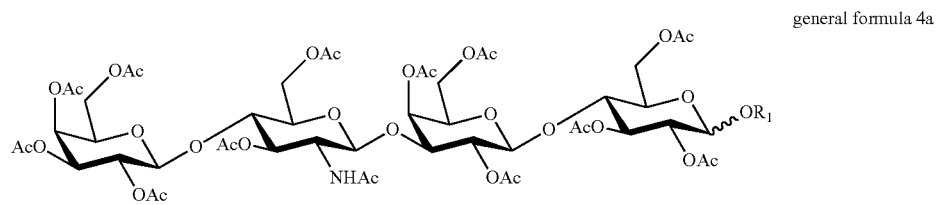

general formula 4a wherein $R_1$ is selected from optionally substituted benzyl, optionally substituted benzhydryl, optionally substituted trityl and optionally substituted naphthylmethyl.

The twelfth aspect of the present invention provides a compound of general formula 5' wherein $R_4$ is optionally substituted acyl, preferably acetyl, —$NR_5R_6$ is —NH-haloacyl, preferably —NH-1-trichloroacetyl or —NH-trifluoroacetyl, and $R_7$ is optionally substituted phenyl, preferably phenyl.

The thirteenth aspect of the present invention relates to a compound of general formula 6'

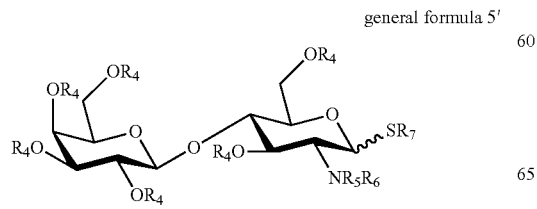

general formula 5'

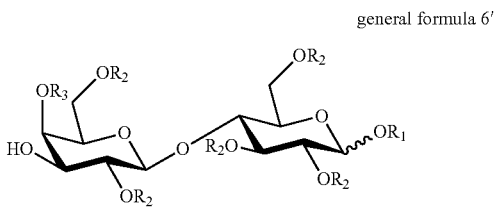

general formula 6' wherein $R_1$ is selected from optionally substituted benzyl, optionally substituted benzhydryl, optionally substituted trityl and optionally substituted naphthylmethyl, $R_2$ is optionally substituted benzoyl, and $R_3$ is selected from optionally substituted acyl and H.

BRIEF DESCRIPTION OF THE FIGURES

The invention will be described in further detail hereinafter with reference to the accompanying figures, in which.

DETAILED DISCLOSURE OF THE INVENTION

Figure 1:
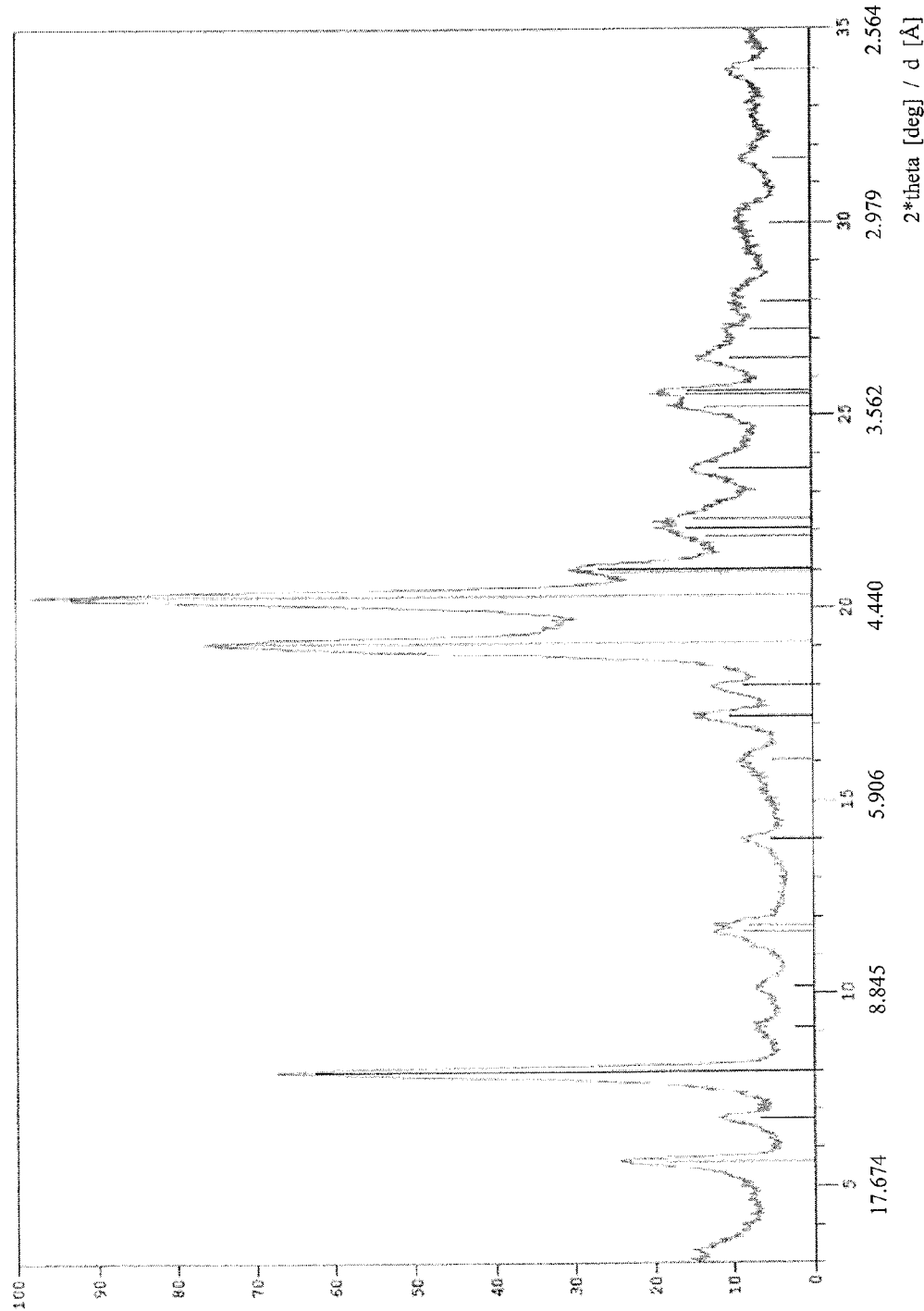
FIG. 1 shows the X-ray powder diffraction pattern of crystalline LNnT prepared according to example 34.

Throughout the present description, the term "alkyl", either alone or when attached to another atom or group, means a linear or branched hydrocarbon group with 1-6 carbon atoms, like methyl, ethyl, n-propyl, i-propyl, n-butyl, i-butyl, s-butyl, t-butyl, etc.

In the present application the term "aryl" refers to homoaromatic groups like phenyl or naphthyl. Preferably, aryl means phenyl.

In the present description, the term "acyl" represent an R—C(=O)—, wherein R may be H, alkyl or aryl, like formyl, acetyl, propionyl, butyryl, pivaloyl, benzoyl, etc. The alkyl and aryl residues both may be substituted.

For the purpose of this specification with claims, the term "optionally substituted" means that the group in question may either carry a substituent or may be unsubstituted.

For the purpose of this specification with claims, the term "substituted" means that the group in question is substituted with a group which typically modifies the general chemical characteristics of the chain or ring. The substituents can be used to modify characteristics of the molecule as a whole, such as stability, solubility, and ability to form crystals. The person skilled in the art will be aware of other suitable substituents of a similar size and charge characteristics, which could be used as alternatives in a given situation.

More generally in connection with the terms "alkyl", "aryl" and "acyl" the term "optionally substituted" is intended to mean that the group in question may be substituted one or several times, preferably 1-5 times, more preferably 1-3 times with group(s) selected from alkyl (only for aryl and aromatic acyl), hydroxy, alkoxy (i.e. alkyl-oxy), carboxy, oxo (forming a keto or aldehyde functionality), alkoxycarbonyl, alkylcarbonyl, formyl, aryl, aryloxy-carbonyl, aryloxy, arylamino, arylcarbonyl, amino, mono- and dialkylamino, carbamoyl, mono- and dialkyl-aminocarbonyl, alkylcarbonylamino, cyano, alkanoyloxy, nitro, alkylthio and halogen (F, Cl, Br, I).

The expression "group removable by catalytic hydrogenation" refers to groups, whose C—O bond is cleaved by addition of hydrogen in the presence of catalytic amounts of palladium, Raney nickel or another appropriate metal catalyst known for use in hydrogenolysis, resulting in the regeneration of the OH group. Groups of this type are well known to the skilled man and thoroughly discussed [e.g. P. G. M. Wuts and T. W. Greene: *Protective Groups in Organic Synthesis*, John Wiley & Sons (2007)]. Suitable groups include benzyl, diphenylmethyl (benzhydryl), 1-naphthylmethyl, 2-naphthylmethyl or triphenylmethyl (trityl) groups, each of which may be optionally substituted by one or more groups selected from: alkyl, alkoxy, phenyl, amino, acylamino, alkylamino, dialkylamino, nitro, carboxyl, alkoxycarbonyl, carbamoyl, N-alkylcarbamoyl, N,N-dialkylcarbamoyl, azido, halogenalkyl or halogen. Preferably, such substitution, if present, is on the aromatic ring(s). Particularly preferred protecting group is benzyl optionally substituted with one or more groups selected from alkyl or halogen. More preferably, the protecting group is selected from unsubstituted benzyl, 4-chlorobenzyl and 4-methylbenzyl. These particularly preferred and more preferable protecting groups have the advantage that the by-products of the hydrogenolysis are exclusively toluene or substituted toluene. Such by-products can easily be removed even in multi ton scales from water soluble oligosaccharide products via evaporation and/or extraction processes.

In connection with the —NH-haloacyl in group —$NR_5R_6$ the term "haloacyl" refers to halogenated acyl groups of formula $C_nH_xX_y$—C(=O)—, wherein integer n is 1, 2 or 3, x+y=2n+1 with the proviso that x<y, and X is F, Cl and Br, such as dichloroacetyl, trichloroacetyl, trifluoroacetyl, heptafluorobutyryl and the like.

The present invention represents a commercial approach suitable for large scale manufacture of LNnT, i.e. typically for the manufacture of batches of at least 1 kg of LNnT, such as at least 5 kg, or at least 50 kg, or even at least 200 kg, e.g. at least 1 ton, of LNnT. The successful strategy is based upon the introduction of relevant crystalline intermediates permitting simple and robust purification methodologies. Crystallization or recrystallization is one of the simplest and cheapest methods to separate a product from contaminations and obtain pure substance. In addition, providing one or more crystalline modifications (polymorphs) of a solid is an important factor in product development, because the different crystalline forms affect the compound's properties—for example thermodynamic stability, solubility, density, hygroscopicity, electrical properties (such as dielectric constant, conductivity), mechanical properties (such as friability, hardness, breaking strength, elasticity), optical properties (such as colour, transparency, refraction), etc.—diversely. It enlarges the repertoire of materials that a scientist has available for improving the product's characteristics.

The present invention provides in a first aspect a method for the preparation of Galpβ1-4GlcNAcpβ1-3Galpβ1-4Glc comprising the steps of:

a) reaction of a donor characterized by general formula 5

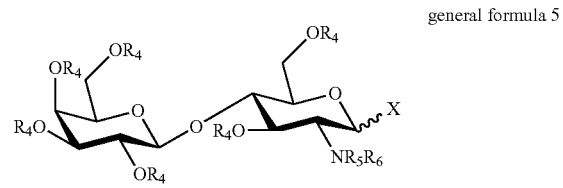

general formula 5

—$NR_5R_6$ is selected from —$NAc_2$, —NH-haloacyl, phthalimide, tetrachlorophthalimide, 2,3-diphenylmaleimide and 2,3-dimethylmaleimide, X is selected from halogen, —OC(=NH)$CCl_3$, —OAc, —OBz and —$SR_7$, wherein $R_7$ is selected from alkyl and optionally substituted phenyl, with an acceptor of general formula 6

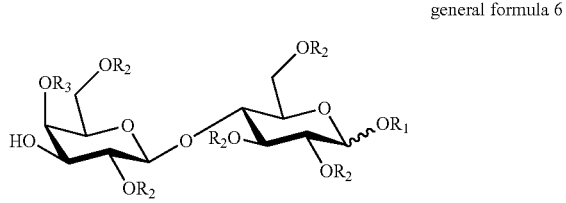

general formula 6 wherein $R_1$ is a group removable by catalytic hydrogenolysis,
$R_2$ is optionally substituted acyl and
$R_3$ is selected from optionally substituted acyl or H,
to yield a compound of general formula 4

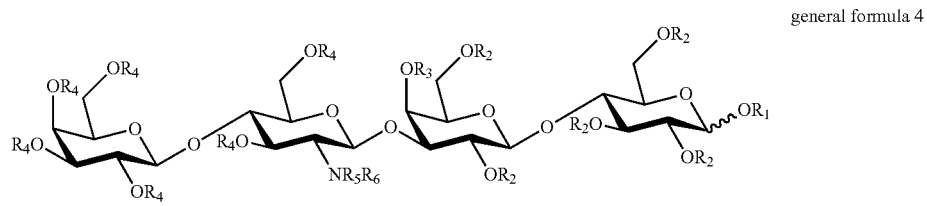

general formula 4 wherein $R_1$, $R_2$, $R_3$, $R_4$ and —$NR_5R_6$ are as defined above,
b) converting the compound of general formula 4 into a compound of general formula 1

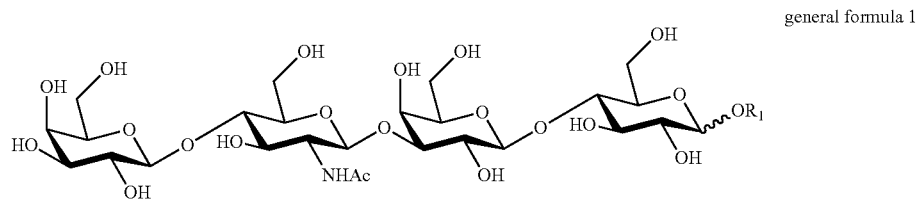

general formula 1 wherein $R_1$ is as defined above,
c) crystallizing the compound of general formula 1, and
d) subsequently subjecting the compound of general formula 1 to catalytic reduction.

With regard to step a) the fully protected LNnT derivatives according to general formula 4 are synthesized in the reaction of a compound of general formula 5 (donor) with a compound of general formula 6 (acceptor) under glycosylation condition.

The coupling of the lactose acceptor of general formula 6 with the lactosaminyl donor of general formula 5 can be carried out an aprotic solvent or in a mixture of aprotic solvents in the presence of an activator (promoter or catalyst) so as to lead to the desired glycosylated product. The new interglycosidic linkage is formed by the nucleophilic displacement of the leaving group X of donor according to general formula 5 with the 3'-OH group of the acceptor according to general formula 6. Other functional groups in both participating reactants have to be masked with protecting groups. In addition the present inventors realized that regioselective glycosylation can be achieved on acceptor of general formula 6, wherein $R_3$ is H. In such dihydroxy acceptors the reactivity of the equatorial 3'-OH and the axial 4'-OH is different: the equatorial OH-group may act as stronger nucleophile under glycosylation conditions. Thus with careful selection of the conditions such as donor reactivity, solvent, temperature, nature of promoter, means of addition of reactants/promoters and like the reaction can be driven to the formation of the desired 1-3 interglycosidic linkage instead of 1-4 coupling. Particular care has to be taken with regard to the stereoselectivity. The stereochemical outcome may be affected by different factors like the presence or absence of a participating group at C-2 of the donor, the nature of the leaving group X, solvent effect, nature of the protective groups on both the donor and acceptor, nature of the promoters or catalysts, temperature, pressure, steric interactions between the donor and acceptor, and like. In case of glucosaminyl or lactosaminyl derivatives an array of anomeric activation for glycosylation is developed and available to a skilled person engaged in carbohydrate chemistry. These methodologies are expansively discussed by reviews and handbooks, for instance by Demchenko (Ed.): Handbook of Chemical Glycosylation, Wiley (2008). For the sake of examples some general considerations are briefly mentioned below depending on the X-group.

The glycosyl halides (X means F, Cl, Br, I) are frequently used in glycosylation reaction because of their easy accessibility and satisfactory reactivity. Typically, anomeric halides follow the reactivity order F<Cl<Br<I for nucleophilic displacement. The glycosylation reactions are generally promoted by heavy metal ion, mainly mercury or silver, and Lewis acids.

Glycosyl trichloroacetimidates (X=—OC(=NH)CCl$_3$) can be easily prepared by the addition of the free anomeric OH to trichloroacetonitrile under inorganic or organic base catalysis. In a typical glycosidation reaction catalytic amount of Lewis acid, such as trimethylsilyl triflate or BF$_3$-etherate, promotes the coupling.

Glycosyl acetates or benzoates (X represents —OAc or —OBz) in glycosylation reaction are first subjected to electrophilic activation providing a reactive intermediate, then treated with the nucleophilic OH-acceptor. Typical activators of choice are Bronsted acids (such as TsOH, HClO$_4$, sulfamic acid), Lewis acids (such as $ZnCl_2$, $SnCl_4$, triflate salts, $BF_3$-etherate, trityl perchlorate, $AlCl_3$, triflic anhydride) and their mixtures.

Thioglycosides (X denotes alkylthio- or phenylthio-group) can be activated by thiofilic promoters such as mercury(II) salts, $Br_2$, $I_2$, NBS, NIS, triflic acid, triflate salts, $BF_3$-etherate, trimethylsilyl triflate, dimethyl-methylthio sulphonium triflate, phenylselenyl triflate, iodonium dicollidine perchlorate, tetrabutylammonium iodide or mixtures thereof; in condensation reactions, preferably by $Br_2$, NBS, NIS and triflate salts.

In a preferred embodiment the glycosyl donor is a compound of general formula 5, wherein $R_4$ is optionally substituted acyl, $—NR_5R_6$ is —NH-haloacyl and X is $—SR_7$, wherein $R_7$ is selected from optionally substituted alkyl or optionally substituted phenyl; more preferably $R_7$ is optionally substituted phenyl; even more preferably $R_4$ is acetyl, $—NR_5R_6$ is selected from —NH-trichloroacetyl and —NH-trifluoroacetyl, $R_7$ is phenyl and $—SR_7$ is in β. The glycosylation is carried out in aprotic solvent(s) like chloroform, dichloromethane, toluene, dioxane, THF, acetonitrile or mixture thereof, preferably chloroform or dichloromethane, under the activation of NIS, NBS, $Br_2$, triflic acid, silver triflate, $BF_3$-etherate or mixture thereof.

In a further preferred embodiment the glycosyl acceptor is a compound of general formula 6, in which $R_1$ is optionally substituted benzyl and $R_3$ is selected from H and optionally substituted benzoyl; more preferably $R_1$ is benzyl, $R_2$ is benzoyl optionally substituted with chloro and $R_3$ is selected from H and benzoyl optionally substituted with chloro, and $OR_1$ is in β.

The donors characterized by general formula 5 can be produced by conventional methodologies known in the art. An approach can imply the galactosylation of the protected glucosamine thioglycoside [e.g. Sherman et al. *Carbohydr. Res.* 2001, 336, 13], or of a methyl glucosaminide derivative [e.g. Kochetkov et al. *Tetrahedron* 1987, 43, 3109]. Another access is based on the derivatization of the double bond of D-lactal hexaacetate, either by azidonitration followed by reduction of the 2-azido group with subsequent protection of the amine formed and nitrate-halogenide exchange on the anomeric carbon [e.g. Lemieux et al. *Can. J. Chem.* 1982, 60, 63], or by nitroso-chlorination followed by acetylation of the formed oxime and diborane reduction [e.g. Ponpipom et al. *Tetrahedron Lett.* 1978, 20, 1717], both methods leading to protected lactosaminyl halogenides. Functionalization of lactosamine is also conceivable (O-acetylation followed by amine protection and anomeric acetate-halogen interconversion). Further anomeric activations can be envisaged by the formation of thioglycosides from halides [e.g. Sherman et al. *Carbohydr. Res.* 2001, 336, 13] or from acetates [e.g. Sato et al. *Tetrahedron Lett.* 1988, 29, 4759]. Another frequently used glycosyl donors are trichloroacetimidates [e.g. Sato et al. *Tetrahedron Lett.* 1988, 29, 4759], and the application of lactosaminyl fluorides—synthesized from the corresponding glycosyl azides—as donors is also published [e.g. Bröder et al. *Carbohydr. Res.* 1993, 249, 221]. The literature examples mentioned above just illustrate some possible pathways without limitation, and the skilled person is capable of combining them to achieve the desired embodiments characterized by general formula 5.

Compounds of general formula 6 are available by the following manipulations. Starting from the common octa-O-acetyl lactose or hepta-O-acetyl lactosyl bromide the corresponding lactoside can be formed with $R_1OH$ under Lewis-acid (e.g. mercury salt, $BF_3$-etherate) activation. By de-O-acetylation (e.g. Zemplén-deprotection, aminolysis or basic hydrolysis) followed by regioselective acetonidation with dimethoxypropane in the presence of acid catalyst the 3',4'-protected lactoside may be obtained, which is then acylated with $R_2$-halogenide or $(R_2)_2O$ (anhydride) under usual conditions. The resulting derivative may be hydrolized with acid to remove isopropylidene giving a diol (compounds of general formula 6, wherein $R_3$ is OH) which is treated with an orthoester derived from $R_3OH$. A cyclic orthoester thus obtained is subsequently rearranged with acid catalyst to another compound of general formula 6, wherein $R_3$ is acyl [see e.g. Paulsen et al. *Carbohydr. Res.* 1985, 137, 39; Lubineau et al. ibid. 1997, 305, 501; and references cited therein] (Scheme 2.).

Scheme 2.

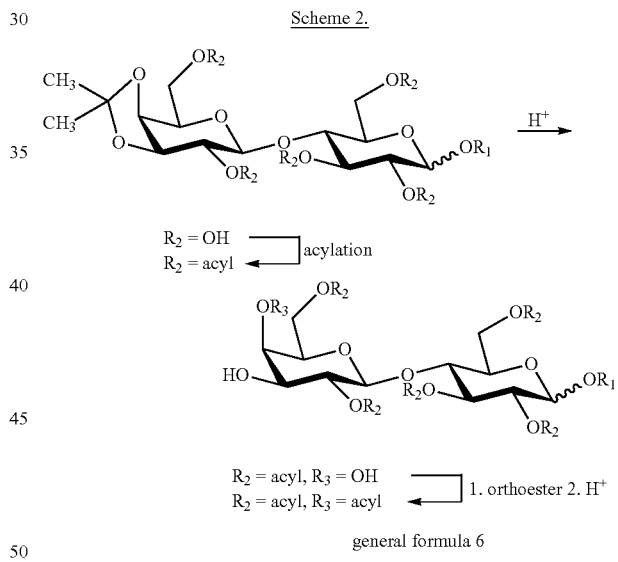

general formula 6

In step b) of the first aspect of the present invention compounds of general formula 4

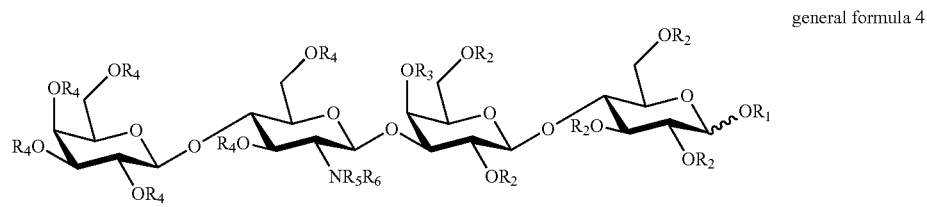

general formula 4 wherein $R_1$ is a group removable by catalytic hydrogenolysis, each of $R_2$ and $R_4$ are independently optionally substituted acyl groups, $R_3$ is selected from optionally substituted acyl or H, $-NR_5R_6$ is selected from $-NAc_2$, $-NH$-haloacyl, phthalimide, tetrachlorophthalimide, 2,3-diphenylmaleimide and 2,3-dimethylmaleimide, are converted into compounds of general formula 1 comprising the steps:

ba) base catalyzed transesterification deprotection or basic hydrolysis of the compound of general formula 4, wherein $-NR_5R_6$ is $-NAc_2$, to give a compound of general formula 1 or bb) base catalyzed transesterification deprotection of a compound of general formula 4, wherein $-NR_5R_6$ is selected from $-NH$-haloacyl, phthalimide, tetrachlorophthalimide, 2,3-diphenylmaleimide and 2,3-dimethylmaleimide, to give a compound of general formula 3 general formula 3

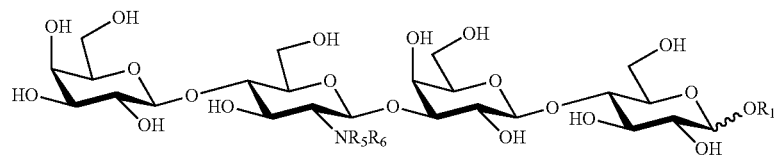

wherein $R_1$ and $-NR_5R_6$ are defined as above, which compound of general formula 3 is subjected to basic hydrolysis or aminolysis to give rise to a compound of general formula 2 general formula 2

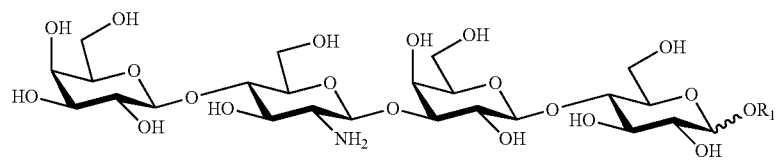

wherein $R_1$ is as defined above, which compound of general formula 2 is converted into the compound of general formula 1, f.

bc) basic hydrolysis of the compound of general formula 4, wherein $-NR_5R_6$ is selected from $-NH$-haloacyl, 2,3-diphenylmaleimide and 2,3-dimethylmaleimide, to give a compound of general formula 2 general formula 2

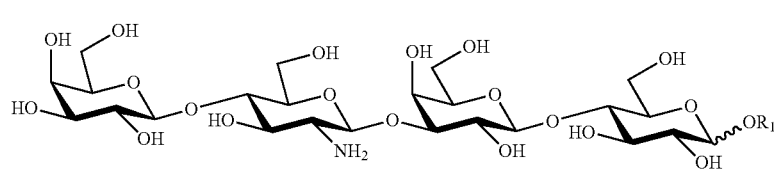

wherein $R_1$ is as defined above, which compound of general formula 2 is converted into the compound of general formula 1, or bd) basic hydrolysis of the compound of general formula 4, wherein $-NR_5R_6$ is selected from phthalimide and tetrachlorophthalimide, followed by aminolysis to give a compound of general formula 2 general formula 2

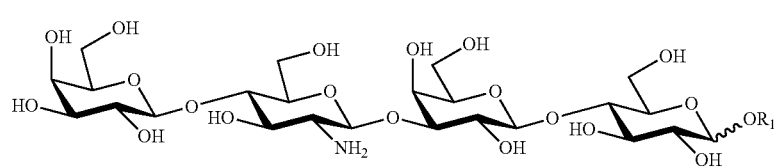

wherein $R_1$ is defined as above, which compound of general formula 2 is converted into the compound of general formula 1, or be) aminolysis of the compound of general formula 4, wherein —$NR_5R_6$ is selected from —$NAc_2$, —NH-haloacyl, phthalimide, tetrachlorophthalimide, 2,3-diphenylmaleimide and 2,3-dimethylmaleimide, to give a compound of general formula 2 general formula 2

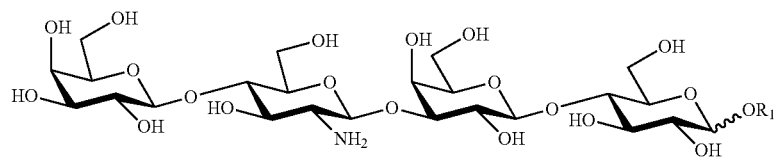

wherein $R_1$ is defined as above, which compound of general formula 2 is converted into the compound of general formula 1.

The term "base catalyzed transesterification deprotection" means a reaction, where the acyl protective groups from hydroxyls are removed in an alcohol solvent such as methanol, ethanol, propanol, t-butanol, etc. in the presence of an alcoholate like NaOMe, NaOEt, KO$^t$Bu, etc. at 20-100° C. temperatures. The alcohol and the alcoholate should be matched. The use of co-solvent as toluene or xylene might be beneficial in order to control particle size of the product and to avoid gel formations. Under this condition only O-acyls can be deprotected or when both $R_5$ and $R_6$ are acetyls, one of the acyl groups is also removed to give a compound having a —NHAc substituent. The —NH-haloacyl and cyclic imide protective groups remain intact under the condition of base catalyzed transesterification deprotection. In a preferred embodiment catalytic amount of NaOMe is used in methanol (Zemplén de-O-acylation).

The term "basic hydrolysis" generally means base catalyzed hydrolysis in water, alcohol or water-organic solvent mixtures, in homogeneous or heterogeneous reaction conditions at temperatures varying from 0-100° C. The base of choice is generally a strong base, e.g. LiOH, NaOH, KOH, Ba(OH)$_2$, K$_2$CO$_3$, basic ion exchange resins, tetraalkylammonium hydroxides, etc. The bases can be used in the form of an aqueous solution as well. This condition affects O-acyls, N-haloacyis, 2,3-diphenylmaleimide and 2,3-dimethylmaleimide. If $R_5$ and $R_6$ are both acetyl, one of the acyl groups is also removed. In a preferred embodiment the base is NaOH and the solvent is methanol.

The term "aminolysis" or N-acyl transfer based deprotection means a treatment with ammonia, hydrazine, substituted hydrazine, ethylene diamine or primary amines in water, alcohol or water-organic solvent mixtures at 20-120° C. temperatures. Under this condition all of the O- and N-protecting acyl groups, including cyclic imides, can be readily removed.

According to another embodiment a compound of general formula 2 obtained is N-acetylated. Selective N-acetylation in the presence of one or more hydroxyls is a well-known reaction and performing such reaction takes part of the skilled person's general knowledge. It involves reaction of the amine with slight excess of acetic anhydride or acetyl chloride ($\approx$1.5-3 equiv.) at about 0-35° C. with or without added base. The eventually formed overacetylated by-product(s) can be readily transformed into the desired compounds of general formula 1 with e.g. NaOH/MeOH or NaOMe/MeOH treatment. In another method, derivatives according to general formula 2 are peracetylated, that is the free amino group and all the free hydroxyl groups are acetylated. It belongs to the skilled person's competence to perform the reaction until all of the groups to be protected are acetylated. The compound is treated with acetic anhydride or acetyl chloride, preferably acetic anhydride, in the presence of a base, preferably pyridine, triethylamine or Hünig's base, to give a group of fully protected tetrasaccharides of general formula 4, which is characterized by general formula 4a general formula 4a

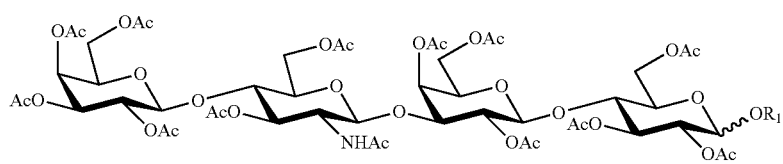

wherein $R_1$ is defined as above. The peracetylated derivative 4a is then subjected to base catalyzed transesterification deprotection or basic hydrolysis (vide supra), preferably to Zemplén de-O-acetylation, to give rise to a compound of general formula 1.

Once compounds of general formula 1 are prepared by taking whatever route specified above, they are isolated in crystalline form. The present inventors are realized that compounds of general formula 1 are crystalline materials. As compounds of general formula 1 are the final intermediates en route to LNnT and the last deprotective step runs practically without by-product formation, their purity is proportional to that of the target product LNnT.

The crystallization is carried out from a solvent system comprising one or more $C_1$-$C_6$ alcohols in the absence of seed crystals. Term "$C_1$-$C_6$ alcohol" refers to alcohols having 1 to 6 carbon atoms, that is methanol, ethanol, n-propanol, i-propanol, t-butanol, i-amylalcohol, etc. Preferably methanol or ethanol is chosen. More preferably the solvent system may further contain water. The water content in the overall volume of the solvent system may preferably range up to 30 v/v %, more preferably 15-25 v/v %.

In a preferred realization 1-O-benzyl LNnT is crystallized form aqueous methanol or ethanol.

In step d) of the first aspect of the present invention a compound of general formula 1 is subjected to catalytic reduction leading to LNnT.

Removal of the $R_1$-group typically takes place in a protic solvent or in a mixture of protic solvents. A protic solvent may be selected from a group consisting of water, acetic acid or $C_1$-$C_6$ alcohol. Mixture of one or more protic solvents with one or more proper aprotic organic solvents miscible partially or fully with the protic solvent(s) (such as THF, dioxane, ethyl acetate, acetone, etc.) may also be applied. Water, one or more $C_1$-$C_6$ alcohols or a mixture of water and one or more $C_1$-$C_6$ alcohols are preferably used as solvent system. Solutions containing the carbohydrate derivatives in any concentration or suspensions of the carbohydrate derivatives with the solvent(s) used are also applicable. The reaction mixture is stirred at 10-100° C. temperature range, preferably between 20-70° C. in hydrogen atmosphere of 1-50 bar in the presence of a catalyst such as palladium, Raney nickel or any other appropriate metal catalyst, preferably palladium on charcoal or palladium black, until reaching the completion of the reaction. Catalyst metal concentrations generally range from 0.1% to 10% based on the weight of carbohydrate. Preferably, the catalyst concentrations range from 0.15% to 5%, more preferably 0.25% to 2.25%. Transfer hydrogenation may also be performed, when the hydrogen is generated in situ from cyclohexene, cyclohexadiene, formic acid or ammonium formate. Addition of organic or inorganic bases/acids and/or basic and/or acidic ion exchange resins can also be used to improve the kinetics of the hydrogenolysis. The use of basic substances is especially preferred when halogen substituents are present on the substituted benzyl moieties of the precursors. Preferred organic bases are including but not limited to triethylamine, diisopropyl ethylamine, ammonia, ammonium carbamate, diethylamine, etc. Preferred organic/inorganic acids are including but not limited to formic acid, acetic acid, propionic acid, chloroacetic acid, dichloroacetic acid, trifluoroacetic acid, HCl, HBr, etc. The conditions proposed above allow simple, convenient and delicate removal of the solvent(s) giving rise to pure LNnT. LNnT can be isolated from the reaction mixture using conventional work-up procedures in crystalline, amorphous solid, syrupy form or concentrated aqueous solution.

In a preferred embodiment 1-O-benzyl LNnT is subjected to catalytic hydrogenolysis to give LNnT. The hydrogenation can be performed in water or in aqueous alcohol, preferably in water/methanol or water/ethanol mixture (alcohol content: 10-50 v/v %) at 15-65° C., preferably between 60-65° C. The concentration of the starting material can vary between 140-230 g/l and the catalyst concentration may range from 0.4% to 1.2% (weight of the metal content based on the weight of the carbohydrate).

Both solid forms of LNnT such as amorphous/freeze dried/spray dried and liquid forms of LNnT such as aqueous solutions/syrups provided by the present invention have high LNnT purity suitable for infant nutritional use including but not limited to infant formulas, infant cereals, clinical infant nutritional products etc. In general, both solid and liquid forms of LNnT produced by the methodologies of the present invention are suitable for general nutritional use for infants, toddlers, children, adults and elderly. Both solid and liquid forms of LNnT provided by the present invention can also be used as food additives, dietary supplements, a component of alcoholic and non alcoholic beverages such as soft drinks, fruit juices, bottled water, wine, beer etc. Both solid and liquid forms of LNnT provided by the present invention can also be used as a therapeutic agent in broad therapeutic application areas including but not limited to prevent bacterial and viral infections, to avoid diarrhoea, to enhance immune system and brain development, etc. Both solid and liquid forms of LNnT provided by the present invention can also be used in veterinary applications including but not limited to fight against infectious diseases of domesticated animals. LNnT provided by the present invention can also be used as a crucial monomer for the preparation of polymeric/polymer mounted products providing multivalent binding for bacteria and viruses. LNnT provided by the present invention can also be used for the preparation of other human milk oligosaccharides by applying chemical and/or enzymatic methodologies including but not limited to simple structural modifications of further fucosylation, further sialylation, further extension of the core structure via N-acetyl lactosaminylation/N-acetylisolactosamylation, etc.

Another aspect of the present invention relates to a novel crystalline polymorph of LNnT. The novel crystalline LNnT comprises X-ray powder diffraction reflections, based on a measurement using CuKα radiation, at 20.32±0.20 2Θ angle, preferably at 20.32±0.20 and 19.10±0.20 2Θ angles, more preferably at 20.32±0.20, 19.10±0.20 and 7.98-0.20 2Θ angles, even more preferably at 20.32±0.20, 19.10±0.20, 7.98±0.20 and 21.03±0.20 2Θ angles, most preferably 20.32±0.20, 19.10±0.20, 7.9810.20, 21.03±0.20 and 20.95±0.20 2Θ angles, in particular 20.32±0.20, 19.10-0.20, 7.9810.20, 21.03±0.20, 20.95±0.20 and 5.66±0.20 2Θ angles. List of peaks of the XRPD pattern of crystalline LNnT prepared according to example 34 is reported in Table 1.

TABLE 1

| 2Θ | rel. intensity |
|---|---|
| 5.66 | 20 |
| 6.78 | 7 |
| 7.98 | 67 |
| 9.10 | 2 |
| 10.16 | 3 |
| 11.58 | 9 |
| 11.76 | 9 |
| 14.00 | 5 |
| 16.07 | 5 |
| 17.20 | 11 |
| 17.98 | 9 |
| 19.10 | 77 |
| 20.32 | 100 |
| 20.95 | 27 |
| 21.03 | 29 |
| 21.88 | 14 |
| 22.08 | 17 |
| 22.32 | 16 |
| 23.62 | 12 |
| 25.22 | 14 |
| 25.57 | 17 |
| 25.64 | 17 |
| 26.50 | 11 |
| 27.25 | 8 |
| 27.94 | 6 |
| 29.99 | 5 |
| 31.66 | 5 |
| 33.94 | 7 |

Figure 3:
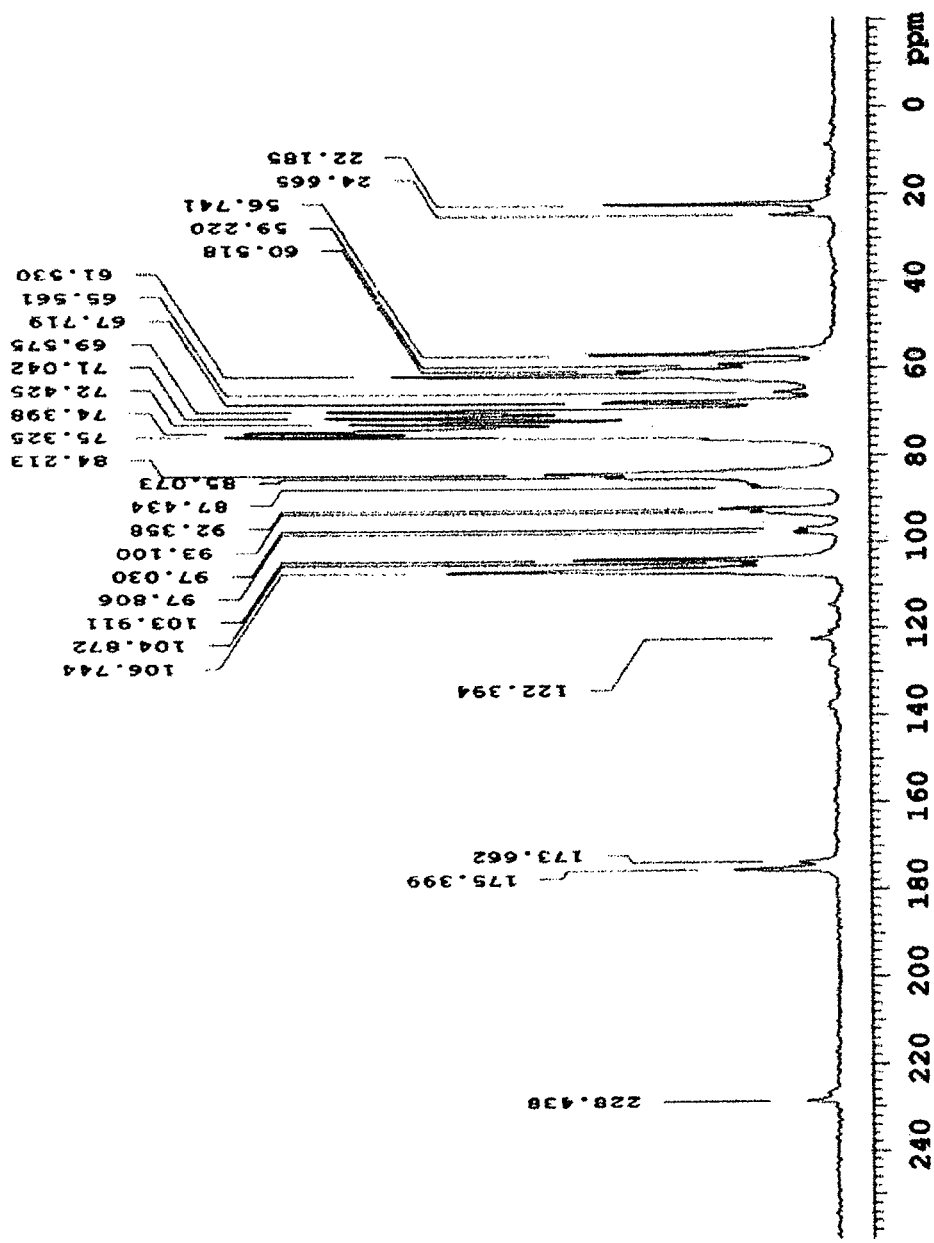
FIG. 3 shows the solid-state $^{13}$C-NMR spectrum of crystalline LNnT prepared according to example 34.

The novel crystalline form of LNnT can be considered as an anomeric mixture of α- and β-anomers or even pure form of one of the anomers. If LNnT is isolated as a polycrystalline material, it forms a mixture of α- and β-anomers, wherein the α-anomer is predominant over the β-anomer (ratio: approx. 5:2) according to solid-state $^{13}$C-NMR measurements (see FIG. 3).

Kuhn et al. [*Chem. Ber.* 1962, 95, 513]1 reported a melting point of 214-218° C. (dec.) for crystalline LNnT. The melting point of LNnT polymorph according to the present invention is 226-230° C. (dec). The remarkable difference between the melting points implies that it concerns different polymorphs.

Figure 2:
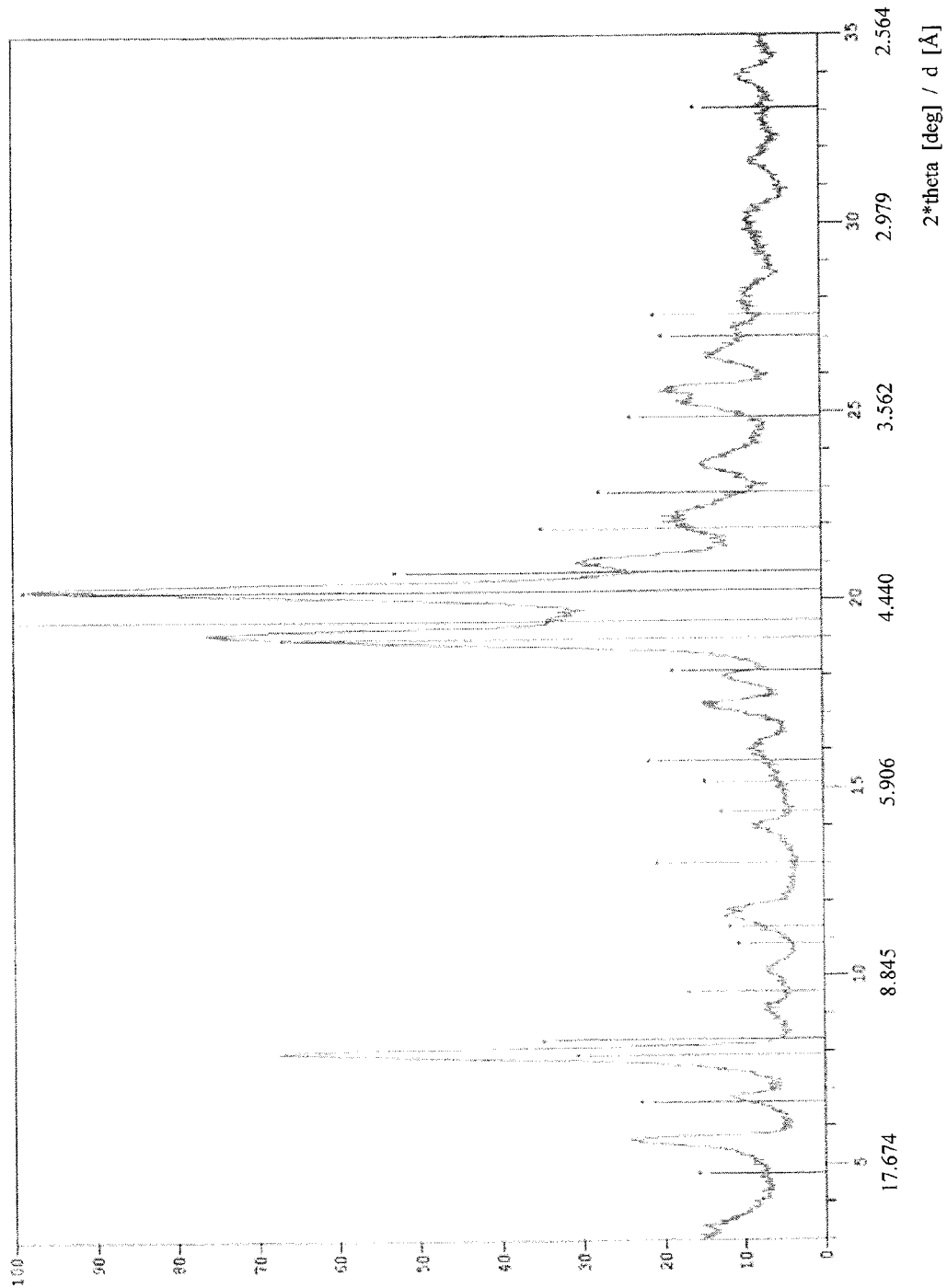
FIG. 2 shows the comparison of X-ray powder diffraction pattern of crystalline LNnT prepared according to 34 and EP-A-1405856 (continuous curve: diffraction pattern of crystalline LNnT prepared according to example 34; vertical lines: data taken from EP-A-1405856).

In European application EP-A-1405856 crystals of LNnT were obtained from aqueous acetone whose powder X-ray diffraction data measured differ significantly from those of the crystals of the present application. Comparison of the data is shown in FIG. 2.

Preferably the crystalline LNnT according to the present invention is substantially free from organic solvent. The expression "substantially free from organic solvent" intends to mean that the content of organic solvent(s) is at most 1000 ppm, preferably at most 800 ppm, more preferably at most 600 ppm, most preferably at most 400 ppm and in particular at most 200 ppm.

According to another preferred embodiment the crystalline LNnT claimed in the present application is substantially pure. The expression "substantially pure" intends to mean that the crystalline LNnT (the novel polymorph) contains less than 10 w/w % of impurity, preferably less than 5 w/w % of impurity, more preferably less than 1 w/w % of impurity, most preferably less than 0.5 w/w % of impurity, in particular less than 0.1 w/w % of impurity, wherein "impurity" refers to any physical entity different to the crystalline LNnT described in the present application, such as amorphous LNnT, different LNnT polymorph(s), unreacted intermediate(s) remained from the synthesis of LNnT, by-product(s), degradation product(s), inorganic salt(s) and/or other contaminations different to organic solvent(s).

The present invention also provides a process for preparing crystalline LNnT by crystallization from a solvent system comprising one or more $C_1$-$C_6$ alcohols. More preferably the solvent system may further contain water. The water content in the overall volume of the solvent system may preferably range up to 40 v/v %. The crystallization preferably can be carried out using 3-15 volumes of the solvent mixture.

In a typical crystallization a solution of LNnT in water/methanol or in water/ethanol, preferably in water/methanol ($\approx$1:1) mixture, taken either from the reaction mixture of the hydrogenation after removing the catalyst or prepared freshly (concentration: 140-180 g/l), is warmed to 50-60° C. to which hot methanol (up to 115-250% of the starting volume) is added in 2-4 portions under stirring and gradual chilling to 35-45° C. The crystallization may be initiated by adding seeding crystals. The resulting warm suspension is then carefully cooled to 0-8° C. and the stirring is optionally continued for 2-5 hours. The crystalline material formed is separated by filtration.

In a further embodiment crystalline LNnT according to the present invention is suitable for pharmaceutical and nutritional use. LNnT alone or in combination with other N-acetyllactosamine and/or fucose and/or sialic acid containing human milk oligosaccharides is particularly effective in the education and/or maturation of the immune system of neonatal infants, and have preventive effect against secondary infections following viral infections such as influenza. The use of LNnT as prebiotic enhances the beneficial effects and efficiency of probiotics, such as *Lactobacillus* and *Bifidobacterium* species, in promoting the development of an early bifidogenic intestinal microbiota in infants, in reducing the risk of development or allergy and/or asthma in infants, in preventing and treating pathogenic infections in such as diarrhoea in infants.

In another aspect, the present invention provides pharmaceutical composition comprising crystalline LNnT claimed as active ingredient and one or more pharmaceutically acceptable carriers including but not limited to additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. The dosage form for administration includes, for example, tablets, powders, granules, pills, suspensions, emulsions, infusions, capsules, syrups, injections, liquids, elixirs, extracts and tincture.

In a further embodiment crystalline LNnT according to the present invention is used for the preparation of pharmaceutical compositions. Pharmaceutical compositions can be manufacture by means of any usual manner known in the art, e.g. described in the most recent edition of Remington's Pharmaceutical Sciences, a standard reference text in the field.

In a further embodiment it is provided nutritional formulations comprising crystalline LNnT according to the present invention such as foods, drinks or feeds. The nutritional formulation may contain edible micronutrients, vitamins and minerals as well. The amounts of such ingredient may vary depending on whether the formulation is intended for use with normal, healthy infants, children, adults or subjects having specialized needs (e.g. suffering from metabolic disorders). Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolized corn-starch, etc.) and proteins from casein, soy-bean, whey or skim milk, or hydrolysates of these proteins, but protein from other source (either intact or hydrolysed) may be used as well. Vitamins may be chosen from the group consisting of vitamin A, B1, B2, B5, B6, B12, C, D, E, H, K, folic acid, inositol and nicotinic acid. The nutritional formula may contain the following minerals and trace elements: Ca, P, K, Na, Cl, Mg, Mn, Fe, Cu, Zn, Se, Cr or I.

In a preferred embodiment the nutritional formulation is an infant formula. Infant formula means a foodstuff intended for particular nutritional use by infants during the first 4-6 months of life and satisfying by itself the nutritional requirements of infants. It may contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet. The infant formula contains crystalline LNnT according to the present invention in a total amount of 0.1-3.0 g/100 g formula.

In another preferred embodiment the nutritional formulation may be a food supplement including crystalline LNnT according to the present invention. The food supplement may comprise one or more probiotics in an amount sufficient to achieve the desired effect in an individual, preferably in children and adults. The food supplement may also contain vitamins, minerals, trace elements and other micronutritients as well. The food supplement may be for example in the form of tablets, capsules, pastilles or a liquid. The supplement may contain conventional additives selected from but not limited to binders, coatings, emulsifiers, solubilising agents, encapsulating agents, film forming agents, adsorbents, carriers, fillers, dispersing agents, wetting agents, jellifying agents, gel forming agents, etc. The daily dose of LNnT ranges from 0.1 to 3.0 g.

According to a more preferred embodiment the food supplement is digestive health functional food as the administration of LNnT provides a beneficial effect on digestive health. Digestive health functional food is a processed food used with intention enhance and preserve digestive health by crystalline LNnT according to the present invention as physiologically functional ingredient or component in forms of tablet, capsule, powder, etc. Different terms such as dietary supplement, nutraceutical, designed food, health product may also be used to refer to functional food.

In a further embodiment crystalline LNnT according to the present invention is used for the preparation of nutritional formulation including foods, drinks and feeds, preferably infant formulas, food supplements and digestive health functional food. The nutritional formulation may be prepared in any usual manner.

Compounds of general formulae 1, 2, 3, 4, 5, and 6 are believed to be valuable synthetic intermediates towards LNnT. The present inventors surprisingly recognized some of the compounds of general formulae 1, 2, 3, 4, 5, and 6 can be obtained in crystalline form. Crystallization or recrystallization is one of the simplest and cheapest methods to isolate a product from a reaction mixture, separate it from contaminations and obtain pure substance. Isolation or purification that uses crystallization makes the whole technological process robust and cost-effective, thus it is advantageous and attractive compared to other procedures. The present invention has a great commercial value in large scale production of LNnT providing high purity of intermediates, which cannot be achieved by any other known purification methods. Although some other intermediates have not shown the ability to crystallize, they can be prepared in clean, high-yielding and less by-product forming reactions where usual work-up (extraction, evaporation, precipitation, etc.) procedures have been sufficient to obtain high purity products which have been used without further purification in the next step.

Thus it is provided valuable LNnT intermediates of general formula 1' general formula 1' general formula 1'

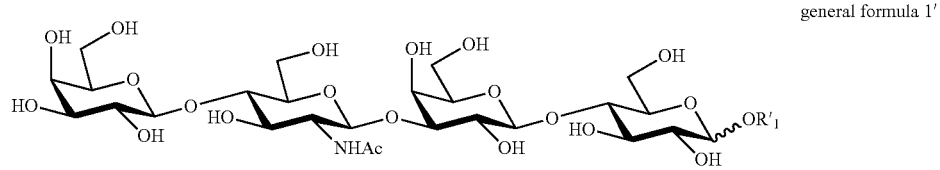

wherein R'$_1$ is selected from substituted benzyl, optionally substituted benzhydryl, optionally substituted trityl and optionally substituted naphthylmethyl.

It is strongly emphasised that novel derivatives characterized by general formula 1' can be considered as sole chemical entities such as either α or β anomers or even an anomeric mixture of α and β isomers, preferably as β-anomer. Novel LNnT intermediates of general formula 1' can be characterized as crystalline solids, oils, syrups, precipitated amorphous material or spray dried products. If crystalline, compounds of general formula 1' might exist either in anhydrous or in hydrated crystalline forms by incorporating one or several molecules of water into their crystal structures. Similarly, novel compounds characterized by general formula 1' might exist as crystalline substances incorporating ligands such as organic molecules and/or ions into their crystal structures.

In a preferred embodiment R'$_1$ is substituted benzyl, preferably 4-chlorobenzyl or 4-methylbenzyl.

Novel compounds of general formula 1' provided by the present invention can be used for the preparation of LNnT itself and other LNnT derivatives by using chemical/enzymatic methodologies known in the Art. Novel compounds of general formulas 1' can also be used as advanced precursors/intermediates for the production/preparation of numerous human milk oligosaccharides. Novel compounds of general formulas 1' can also be considered as valuable intermediates for the synthesis of complex oligosacharides/glycoconjugates suitable for therapeutic/nutritional use.

It is provided valuable LNnT intermediates of general formula 2' general formula 2'

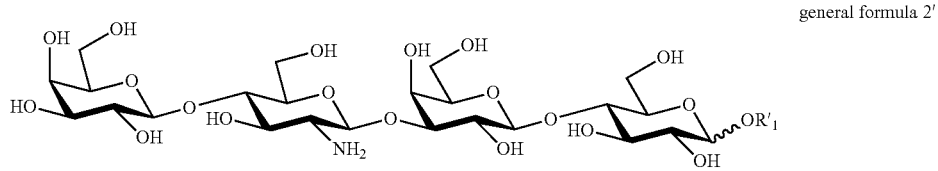

wherein R'$_1$ is selected from substituted benzyl, optionally substituted benzhydryl, optionally substituted trityl and optionally substituted naphthylmethyl.

It is strongly emphasised that novel derivatives characterized by general formula 2' can be considered as sole chemical entities such as either α or β anomers or even an anomeric mixture of α and β isomers, preferably as β-anomer. Novel LNnT intermediates of general formula 2' can be characterized as crystalline solids, oils, syrups, precipitated amorphous material or spray dried products. If crystalline, compounds of general formula 2' might exist either in anhydrous or in hydrated crystalline forms by incorporating one or several molecules of water into their crystal structures. Similarly, novel compounds characterized by general formula 2' might exist as crystalline substances incorporating ligands such as organic molecules and/or ions into their crystal structures.

In a preferred embodiment R'$_1$ is substituted benzyl, preferably 4-chlorobenzyl or 4-methylbenzyl.

Novel compounds of general formula 2' provided by the present invention can be used for the preparation of LNnT itself and other LNnT derivatives by using chemical/enzymatic methodologies known in the Art. Novel compounds of general formulas 2' can also be used as advanced precursors/ intermediates for the production/preparation of numerous human milk oligosaccharides. Novel compounds of general formulas 2' can also be considered as valuable intermediates for the synthesis of complex oligosaccharides/glycoconjugates suitable for therapeutic/nutritional use.

Furthermore it is provided compounds of general formula 3

Novel compounds of general formula 3 provided by the present invention can be used for the preparation of LNnT itself and other LNnT derivatives by using chemical/enzymatic methodologies known in the Art. Novel compounds of general formulas 3 can also be used as advanced precursors/ intermediates for the production/preparation of numerous human milk oligosaccharides. Novel compounds of general formulas 3 can also be considered as valuable intermediates for the synthesis of complex oligosaccharides/glycoconjugates suitable for therapeutic/nutritional use.

Moreover it is provided compounds of general formula 4' general formula 3

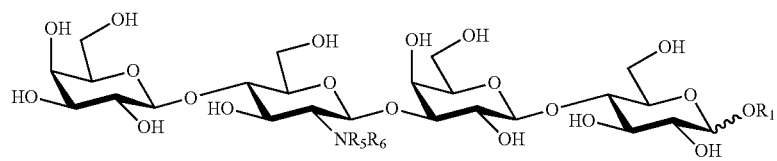

general formula 4'

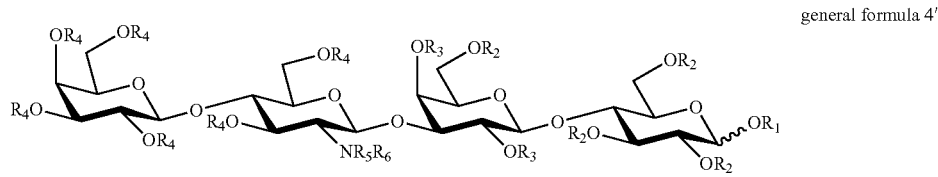

wherein R$_1$ is selected from optionally substituted benzyl, optionally substituted benzhydryl, optionally substituted trityl and optionally substituted naphthylmethyl, and —NR$_5$R$_6$ is selected from —NH-haloacyl, phthalimide, tetrachlorophthalimide, 2,3-diphenylmaleimide and 2,3-dimethylmaleimide.

It is strongly emphasised that novel derivatives characterized by general formula 3 can be considered as sole chemical entities such as either α or β anomers or even an anomeric mixture of α and β isomers, preferably as β-anomer. Novel LNnT intermediates of general formula 3 can be characterized as crystalline solids, oils, syrups, precipitated amorphous material or spray dried products. If crystalline, compounds of general formula 3 might exist either in anhydrous or in hydrated crystalline forms by incorporating one or several molecules of water into their crystal structures. Similarly, novel compounds characterized by general formula 3 might exist as crystalline substances incorporating ligands such as organic molecules and/or ions into their crystal structures.

In a preferred embodiment R$_1$ is selected from benzyl, 4-methylbenzyl and 4-chlorobenzyl, preferably benzyl and —NR$_5$R$_6$ is —NH-haloacyl, preferably —NH-trichloroacetyl.

wherein R$_1$ is selected from optionally substituted benzyl, optionally substituted benzhydryl, optionally substituted trityl and optionally substituted naphthylmethyl, and each of R$_2$ and R$_4$ are independently optionally substituted acyl, R$_3$ is selected from optionally substituted acyl and H, —NR$_5$R$_6$ is selected from —NAc$_2$, —NH-haloacyl, tetrachlorophthalimide, 2,3-diphenylmaleimide and 2,3-dimethylmaleimide.

It is strongly emphasised that novel derivatives characterized by general formula 4' can be considered as sole chemical entities such as either α or β anomers or even an anomeric mixture of α and β isomers, preferably as β-anomer. Novel LNnT intermediates of general formula 4' can be characterized as crystalline solids, oils, syrups, precipitated amorphous material or spray dried products. If crystalline, compounds of general formula 4' might exist either in anhydrous or in hydrated crystalline forms by incorporating one or several molecules of water into their crystal structures. Similarly, novel compounds characterized by general formula 4' might exist as crystalline substances incorporating ligands such as organic molecules and/or ions into their crystal structures.

In a preferred embodiment R$_1$ is selected from benzyl, 4-methylbenzyl and 4-chlorobenzyl, preferably benzyl, R$_2$ is benzoyl optionally substituted by chloro, R$_3$ is optionally substituted benzoyl, preferably benzoyl, R$_4$ is acetyl and —NR$_5$R$_6$ is —NH-haloacyl, preferably —NH-trichloroacetyl.

Novel compounds of general formula 4' provided by the present invention can be used for the preparation of LNnT itself and other LNnT derivatives by using chemical/enzymatic methodologies known in the Art. Novel compounds of general formulas 4' can also be used as advanced precursors/intermediates for the production/preparation of numerous human milk oligosaccharides. Novel compounds of general formulas 4' can also be considered as valuable intermediates for the synthesis of complex oligosaccharides/glycoconjugates suitable for therapeutic/nutritional use.

Moreover it is provided compounds of general formula 4a general formula 4a

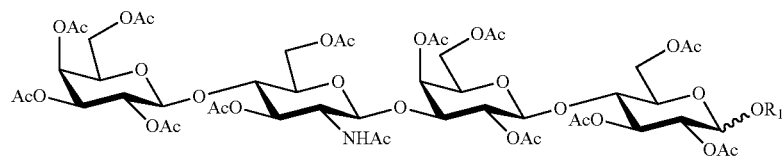

wherein $R_1$ is selected from optionally substituted benzyl, optionally substituted benzhydryl, optionally substituted trityl and optionally substituted naphthylmethyl.

It is strongly emphasised that novel derivatives characterized by general formula 4a can be considered as sole chemical entities such as either α or β anomers or even an anomeric mixture of α and β isomers, preferably as β-anomer. Novel LNnT intermediates of general formula 4a can be characterized as crystalline solids, oils, syrups, precipitated amorphous material or spray dried products. If crystalline, compounds of general formula 4a might exist either in anhydrous or in hydrated crystalline forms by incorporating one or several molecules of water into their crystal structures. Similarly, novel compounds characterized by general formula 4a might exist as crystalline substances incorporating ligands such as organic molecules and/or ions into their crystal structures.

In a preferred embodiment $R_1$ is selected from benzyl, 4-methylbenzyl and 4-chlorobenzyl, preferably benzyl.

Novel compounds of general formula 4a provided by the present invention can be used for the preparation of LNnT itself, especially when selective N-acetylation of the compounds of general formula 2 is not efficient, and other LNnT derivatives by using chemical/enzymatic methodologies known in the Art. Novel compounds of general formulas 4a can also be used as advanced precursors/intermediates for the production/preparation of numerous human milk oligosaccharides. Novel compounds of general formulas 4a can also be considered as valuable intermediates for the synthesis of complex oligosaccharides/glycoconjugates suitable for therapeutic/nutritional use.

Another aspect of the invention relates to the novel crystalline lactosaminyl donor characterized by the general formula 5' general formula 5'

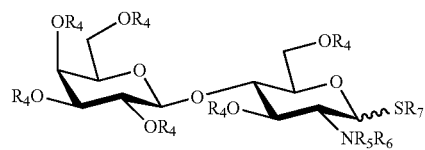

wherein $R_4$ is optionally substituted acyl, —$NR_5R_6$ is —NH-haloacyl, and $R_7$ is optionally substituted phenyl.

It is strongly emphasised that novel derivatives characterized by general formula 5' can be considered as sole chemical entities such as either α or β anomers or even an anomeric mixture of α and β isomers, preferably as β-anomer. Novel LNnT intermediates of general formula 5' can be characterized as crystalline solids, oils, syrups, precipitated amorphous material or spray dried products. If crystalline, compounds of general formula 5' might exist either in anhydrous or in hydrated crystalline forms by incorporating one or several molecules of water into their crystal structures. Similarly, novel compounds characterized by general formula 5' might exist as crystalline substances incorporating ligands such as organic molecules and/or ions into their crystal structures.

In preferred embodiments $R_4$ is acetyl, —$NR_5R_6$ is —NH-trichloroacetyl or —NH-trifluoroacetyl, $R_7$ is phenyl and —$SR_7$ in β.

Compounds of general formula 5' are stable, can be stored for longer period of time without significant decomposition, can be easily activated in glycosylation reactions and shows excellent β-selectivity. As other β-selective lactosaminyl donors are known not to be solid and/or stable, compounds of general formula 5' according to the present application has obviously advantageous applicability in lactosaminylation reactions and thus represent a valuable donor tool in syntheses where lactosamine containing oligosaccharides are targeted, especially in large or industrial scale.

Compounds of general formula 5' can be prepared as follows: lactosamine hydrochloride is acetylated in $Ac_2O/HBr/AcOH$ to give 1,3,6,2',3',4'6'-hepta-O-acetyl-lactosamine hydrochloride which is N-acylated with haloacyl halogenide or anhydride to the —NH-haloacyl derivative. Bromosugar formation with HBr/AcOH followed by thiolysis with $R_7SH$ thiophenol derivative readily gives compounds of general formula 5'. The acetyl groups can be changed to other appropriate acyl groups by base catalyzed transesterification reaction followed by subsequent acylation.

The present invention thus provides the valuable compounds of general formula 6' general formula 6'

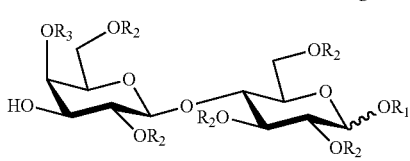

wherein $R_1$ is selected from optionally substituted benzyl, optionally substituted benzhydryl, optionally substituted trityl and optionally substituted naphthylmethyl, $R_2$ is optionally substituted benzoyl, and $R_3$ is selected from optionally substituted benzoyl and H.

The preferred embodiments encompass compounds of general formula 6', wherein $R_1$ is optionally substituted benzyl, preferably benzyl, 4-methylbenzyl or 4-chlorobenzyl, $R_2$ is optionally substituted benzoyl, preferably benzoyl or 4-chlorobenzoyl, and $R_3$ means benzoyl or H.

The present inventors realized that acetyl group as $R_3$ are inconvenient protective group when compounds of general formula 6 act as glycosyl acceptor in glycosidation reactions. Under the conditions of coupling acetyl migration always occurred to give complex mixture containing substances with similar physical characteristics which compounds can be separated only by lengthy and/or sophisticated and/or laborious techniques, e.g. chromatography. Choosing bulkier acyl protective group that don't tend or tend less to migrate results in an acceptor whose coupling product is formed almost exclusively in glycosidation, making the work-up procedure and isolation process of the desired compounds simpler, quick, powerful and cost-effective, e.g. by crystallization, which is one of the paramount concerns in large scale preparation or industrial process.

Other features of the invention will become apparent in the course of the following descriptions of exemplary embodiments which are given for illustration of the invention and are not to be limiting thereof.

EXAMPLES

Example 1

Suspension of 10 g of benzyl β-D-lactoside in acetone (50 ml), dimethoxypropane (3.5 ml) and TMSCl (7 ml) was stirred at rt for 5 h. The mixture was diluted with ethyl acetate (50 ml), filtered, and the cake was washed with ethyl acetate (2×30 ml). The wet cake was dissolved in pyridine (36 ml) and dry DCM (50 ml) and 4-chlorobenzoyl chloride (22 ml) was added slowly to maintain the temperature between 40-45° C. After overnight stirring methanol (10 ml) and DCM (10 ml) were added and extractive work-up was made (2×1M HCl, 1× water, 1×sat. $NaHCO_3$). The combined organic phase was concentrated and as thick syrup it was poured to 50 ml of isopropanol under intensive stirring. The solid was filtered, washed with isopropanol and dried to result in 20.0 g of benzyl 2,3,6,2',6'-penta-O-(4-chlorobenzoyl)-3',4'-di-O-isopropylidene-β-D-lactoside (72%). $[\alpha]_D$=+58.4° (c=1 DCM), Mp: 184° C.

Example 2

10 g of benzyl 2,3,6,2',6'-penta-O-(4-chlorobenzoyl)-3',4'-di-O-isopropylidene-β-D-lactoside was dissolved in DCM (20 ml), acetonitrile (2 ml) and 50% $HClO_4$ (1 ml) and the mixture was stirred at rt for 30 min. The solution was extracted with sat. $NaHCO_3$ (2×10 ml), dried, filtered and concentrated. The obtained material was redissolved in ethyl acetate (10 ml) and diluted with hexane (50 ml). The suspension was stirred at rt for 30 min, the filtered to yield 5.4 g of benzyl 2,3,6,2',6'-penta-O-(4-chlorobenzoyl)-β-D-lactoside as white crystals. $[\alpha]_D$=+58.65° (c=1 DCM), Mp: 200-201° C.

Example 3

Analogously prepared with propionyl chloride according to examples 1 and 2: benzyl 2,3,6,2',6'-penta-O-propionyl-β-D-lactoside.

$^1$H NMR (CDCl$_3$, 300 MHz) δ: 7.346-7.227 (5H, Ph), 5.140 (1H, dd, J=9.1, 9.7, 1H-3), 4.980 (1H, dd, J=7.9, 9.7, H-2), 4.881 (1H, dd, J=7.9 9.7, H-2'), 4.838 (1H, d, J=12.3, ½C$\underline{H}_2$Ph), 4.570 (1H, d, J=12.3, ½C$\underline{H}_2$Ph), 4.495 (1H, dd, J=1.8, 11.7, H-6a or H-6a'), 4.343-4.282 (2I-1, unresolved, H-6a or H-6a', H-1), 4.217-4.155 (2H, unresolved, H-6b, H-6b'), 3.821 (1H, d, J=3.4, H-4'), 3.743 (1H, dd, J=9.8, 9.8, H-4), 3.606-3.537 (3H, unresolved, H-3', H-5, Ht-5'), 2.438-2.194 (10H, m, 5×C$\underline{H}_2$CH$_3$), 1.263-1.036 (15H, m, 5×CH$_2$C$\underline{H}_3$).

$^{13}$C NMR (CDCl$_3$, 75.4 MHz) δ: 174.7, 174.3, 173.9, 173.8, 172.9, 171.2 (6×CO), 136.6-127.9 (Ph), 100.6 (C-1'), 99.1 (C-1), 75.9 (C-4), 73.3, 72.9, 72.7, 72.3, 72.2 (C-2', C-3, C-3', C-5, C-5'), 71.2 (C-2), 70.6 (C$\underline{H}_2$Ph), 68.4 (C-4'), 62.2, 62.0 (C-6, C-6').

Example 4

Analogously prepared with benzoyl chloride according to examples 1 and 2: benzyl 2,3,6,2',6'-penta-O-benzoyl-β-D-lactoside.

$^1$H NMR. (CDCl$_3$) δ: 8.20-7.10 (m, 30H, aromatic), 5.55 (dd, 1 H, $J_{2,3}$ 9.82 Hz, $J_{3,4}$ 9.82 Hz, H-3), 5.49 (dd, 1 H, $J_{1,2}$ 9.78 Hz, H-2), 5.35 (dd, 1 H, $J_{1',2'}$ 7.85 Hz, $J_{2',3'}$ 9.64 Hz, H-2'), 4.81 and 4.57 (ABq, 2 H, $J_{gem}$ 12.59 Hz, —C$\underline{H}_2$Ph), 4.62 (d, 1 H, H-1), 4.57 (d, 1 H, H-1'), 4.52 (m, 2 H, H-6), 4.12 (m, 1 H, H-4), 3.80 (m, 1 H, H-4'), 3.75 (m, 1 H, H-5), 3.70 (m, 1 H, H-3').

$^{13}$C NMR (CDCl$_3$) δ: 166.51, 166.31, 166.18, 166.16 and 165.45 (5×CO), 101.23 (C-1'), 99.09 (C-1), 76.49 (C-4), 73.81 (C-2'), 73.26, 73.22, 73.19 and 72.87 (C-3, C-5, C-3' and C-5'), 72.80 (C-2), 71.77 (—C$\underline{H}_2$Ph), 68.81 (C-4'), 62.85 and 61.99 (C-6 and C-6').

Example 5

Analogously prepared from 4-methylbenzyl β-D-lactoside according to examples 1 and 2: 4-methylbenzyl 2,3,6,2',6'-penta-O-(4-chlorobenzoyl)-β-D-lactoside.

$^1$H NMR (CDCl$_3$): 7.8, 7.4, 7.2, 7.0 (m), 5.4 (m, 3H), 4.76 (d, 1H), 4.5 (m, 5H), 4.1 (dd, 1H), 4.0 (m, 2H), 3.84 (m, 11H), 3.72 (m, 2H), 3.6 (m, 2H), 3.48 (m, 1H), 3.3 (d, 1H-1).

$^{13}$C NMR (CDCl$_3$): 165.3, 165.2, 165.1, 164.3, 139.9, 139.8, 137.9, 133.2, 131.3, 131.1, 130.9, 130.9, 129.1, 129.0, 128.9, 128.8, 128.7, 128.1, 127.9, 127.8, 127.7, 127.5, 127.4, 101.1, 98.3, 76.4, 73.6, 73.4, 72.9, 72.6, 72.3, 71.7, 70.4, 68.6, 62.9, 62.0, 60.4, 21.1, 14.2.

Example 6

To a mixture of 116.6 g of compound according to example 2 in toluene (600 ml) trimethyl ortobenzoate (120 ml) and camphenesulphonic acid (4 g) were added. The mixture was stirred vigorously at rt for 3 h, then 80% acetic acid (160 ml) was added. After further 1 h of stirring the biphasic mixture obtained was separated, the organic phase was diluted with toluene (600 ml), washed with water (800 ml) and sat. $NaHCO_3$ (2×600 ml), dried, filtered and evaporated. The resulting oil was dropped into 600 ml of heptane and seeded. The white crystalline compound was filtered, washed and dried to yield 110.3 g of acceptor (a compound of general formula 6, wherein $R_1$=Bn, $R_2$=4-chlorobenzoyl, $R_3$=benzoyl, $OR_1$ in β). $[\alpha]_D$=+17.13° (c=1 DCM), Mp 156-157° C.

Example 7

Analogously prepared from compound of example 4: a compound of general formula 6, wherein $R_1$=Bn, $R_2$=$R_3$=benzoyl, $OR_1$ in β.

$^1$H NMR. (CDCl$_3$) δ: 8.20-7.00 (m, 35 H, aromatic), 5.67 (dd, 1 H, $J_{2,3}$ 9.77 Hz, $J_{3,4}$ 9.11 Hz, H-3), 5.55 (dd, 1 H, $J_{1,2}$ 7.81 Hz, H-2), 5.47 (dd, 1 H, $J_{3',4'}$ 3.45 Hz, $J_{4',5'}$<1 Hz, H-4'), 5.30 (dd, 1 H, $J_{1',2'}$ 7.82 Hz, $J_{2',3'}$ 9.97 Hz, H-2'), 4.85 and 4.60 (ABq, 2 H. $J_{gem}$ 12.59 Hz, —C$\underline{\text{H}}_2$Ph), 4.72 (d, 1 H, H-1), 4.70 (d, 1 H, H-1'), 4.60 (m, 2 H, H-6), 4.21 (m, 1 H, H-4), 3.93 (m, 1 H, H-3'), 3.82 (m, 1 H, H-5), 3.75-3.45 (m, 3 H, H-5' and H-6) 2.70 (d, 1 H, $J_{3',OH}$ 6.68 Hz, 3'-OH).

$^{13}$C NMR (CDCl$_3$) δ: 166.67, 166.26, 166.03, 165.90, 165.68 and 165.41 (6×CO), 100.79 (C-1'), 99.35 (C-1), 76.16 (C-4), 73.89 (C-2'), 73.26 (C-5), 72.96 (C-3), 72.11 (C-3'), 71.79 (C-2), 71.76 (C-5'), 70.73 (—$\underline{\text{C}}$H$_2$Ph), 70.22 (C-4'), 62.87 and 61.68 (C-6 and C-6').

Example 8

Analogously prepared from compound of example 5: a compound of general formula 6, wherein R$_1$=4-methylbenzyl, R$_2$=4-chlorobenzoyl, R$_3$=benzoyl, OR$_1$ in β.

$^1$H-NMR (CDCl$_3$): 7.92-7.0 (m, aromatic H), 5.6 (dd, 1H), 5.5 (d, 1H), 5.41 (dd, 1H), 5.3 (dd, 1H), 4.8 (d, 1H), 4.68 (m, 2H), 4.52 (m, 2H), 4.08 (m), 4.0 (m, 2H), 3.78 (m, 31-1H), 3.6 (m, 1H).

$^{13}$C NMR (CDCl$_3$): 165.7, 165.2, 165.1, 164.7, 164.5, 164.3 (Bz and ClBz carbonyls), 140.1, 140.02, 139.9, 139.7, 139.6, 137.8, 133.7, 133.1, 131.2-127.2 aromatic carbons, 100.6, 98.6 (anomeric carbons), 75.9, 73.6, 73.1, 72.9, 71.7, 71.4, 71.3, 70.5, 69.9, 62.9, 61.7, 45.9, 42.7, 42.4, 14.1.

Example 9

Analogously prepared from 4-chlorobenzyl β-D-lactoside according to examples 1, 2 and 6: a compound of general formula 6, wherein R$_1$=4-chlorobenzyl, R$_2$=4-chlorobenzoyl, R$_3$=benzoyl OR$_1$ in β.

$^1$H NMR (CDCl$_3$): 7.89-7.0 (m, aromatic H), 5.63 (dd, 1H), 5.5 (d, 1H), 5.42 (dd, 1H), 5.28 (dd, 1H), 4.78 (d, 1H), 4.68 (dd, 1H), 4.54 (m, 3H), 4.1 (m, 2H), 3.98 (m, 1H), 3.8 (m, 2H), 3.6 (m, 2H).

$^{13}$C NMR (CDCl$_3$): 165.8, 165.2, 164.8, 164.5, 164.3, 140.2, 140.0, 139.8, 134.9, 133.9, 133.8, 131.2, 131.1, 130.9, 130.9, 130.8, 129.9, 129.0, 128.9, 128.8, 128.7, 128.6, 128.5, 127.7, 127.4, 127.3, 100.6, 99.2, 75.8, 73.6, 73.0, 71.8, 71.5, 71.4, 70.0, 69.9, 62.8, 61.6, 57.9, 56.1, 48.1, 46.0, 42.7, 42.5.

Example 10

10 g of lactosamine hydrochloride was dissolved Ac$_2$O (50 ml) and 10 ml of 30% HBr/AcOH was added at 0° C. The reaction mixture was allowed to warm to rt, stirred for 10 h and poured into 200 ml of tert-butyl methyl ether (MTBE). The precipitation was filtered, washed with MTBE and dried to give 12.4 g of 1,3,6,2',3',4'6'-hepta-O-acetyl-lactosamine hydrochloride as light brown powder. $^1$H NMR (CDCl$_3$) δ: 5.57 and 5.22 (2 m, 1 H, H-1 α and β), 5.57, 5.29, 4.98 and 4.89 (4 m, each 1 H, H-3, H-2', H-3' and H-4'), 4.41 (1 H, H-1'), 4.37 and 4.06 (2 m, 1 H and 3 H, H-6 and H-6'), 3.83, 3.82 and 3.73 (3 in, each I H, H-4, H-5 and H-5'), 3.40 (m, 1 H, 1 H-2), 2.10, 2.10, 2.06, 2.04, 1.98, 1.90 and 1.89 (7 s, each 3 H, 7×-OAc). $^{13}$C NMR (CDCl$_3$) δ: 100.87 (C-1'), 92.91 and 88.93 (C-1 α and β), 75.64, 73.03 and 71.01 (C-4, C-5 and C-5'), 61.72 and 60.72 (C-6 and C-6'), 54.08 (C-2).

Example 11

16.4 g of 1,3,6,2',3',4'6'-hepta-O-acetyl-lactosamine hydrochloride was dissolved in DCM (30 ml) and cooled to 0° C. First 2.95 ml of trichloroacetyl chloride then slowly 7.6 ml of triethyl amine were added and the stirring was continued for 30 min at 0° C. The reaction mixture was diluted with DCM (10 ml), washed with water (2×20 ml) and brine (20 ml), dried on Na$_2$SO$_4$ and filtered. A mixture of this solution with Ac$_2$O (100 μl) was dropped to a solution of DCM (15 ml), HBr/AcOH (15 ml) and Ac$_2$O (1 ml) at 0° C. and was kept in the same temperature for 30 min. The reaction mixture was diluted with DCM (10 ml), washed with cold water (3×20 ml) and cold sat. NaHCO$_3$ (20 ml). To the organic phase 100 ml of half sat. Na$_2$CO$_3$ solution, 4.3 ml of thiophenol and 100 mg of tetrabutyl ammonium hydrogensulphate were added and the biphasic mixture was stirred at rt for 30 min. After separation the organic phase was washed with brine (2×20 ml), and after addition of ethyl acetate (50 ml) the crystal formed was filtered (6.3 g). From the concentrated mother liquor further 3.2 g of crystal was precipitated by adding MTBE (50 ml). Combined yield: 9.5 g of product (a compound of general formula 5, wherein R$_4$=acetyl, —NR$_5$R$_6$=—NH-trichloroacetyl, X=β-SPh). $^1$H NMR. (CDCl$_3$) δ: 7.50 and 7.30 (2 m, 5 H, aromatic), 7.08 (d, 1 H, $J_{NH,2}$ 9.37 Hz, NH), 5.33 (dd, 1 H, $J_{3',4'}$ 3.19 Hz, $J_{4',5'}$ 0.65 Hz, H-4'), 5.21 (dd, 1 H, $J_{2,3}$ 8.34 Hz, $J_{3,4}$ 10.12 Hz, 1 H-3), 5.08 (dd, 1 H, $J_{1',2'}$ 7.83 Hz, $J_{2',3'}$ 10.47 Hz, H-2'), 4.94 (dd, 1H, H-3'), 4.75 (d, 1 H, $J_{1,2}$ 10.34 Hz, H-1), 4.55 and 4.09 (2 m, 4 H, H-6 and H-6'), 4.47 (d, 1H, H-1'), 4.00 (min, 1 H, H-2), 3.87, 3.78 and 3.67 (3 m, each 1 H, Ht-4, H-5 and H-5'), 2.16, 2.11, 2.10, 2.04, 2.03 and 1.96 (6 s, each 3 H, 6×-OAc). $^{13}$C NMR (CDCl$_3$) δ: 100.47 (C-1'), 85.1 (C-1), 75.99, 75.41 and 69.97 (C-4, C-5 and C-5'), 72.50 (C-3), 70.17 (C-3'), 68.42 (C-2'), 65.87 (C-4'), 61.43 and 60.26 (C-6 and C-6'), 53.66 (C-2), 21.35, 21.11, 21.11, 20.98, 20.87 and 20.75 (6×OAc). Mp.: 247-249° C., $[α]_D$=−13.9° (c=0.58 CHCl$_3$).

Example 12

Similarly prepared according to example 11: compound of general formula 5, wherein R$_4$=acetyl, —NR$_5$R$_6$=—NH-dichloroacetyl, X=β-SPh.

$^1$H NMR (CDCl$_3$) δ: 7.50 and 7.30 (2 nm, 5 H, aromatic), 7.08 (d, 1 H, $J_{NH,2}$ 9.37 HHz, NH), 5.33 (dd, 1 H, $J_{3',4'}$ 3.19 Hz, $J_{4',5'}$ 0.65 Hz, H-4'), 5.21 (dd, 1 H, $J_{2,3}$ 8.34 Hz, $J_{3,4}$ 10.12 Hz, H-3), 5.08 (dd, 1 H, $J_{1',2'}$ 7.83 Hz, $J_{2',3'}$ 10.47 Hz, H-2'), 4.94 (dd, 1 H, H-3'), 4.75 (d, 1 H, $J_{1,2}$ 10.34 Hz, H-1), 4.55 and 4.09 (2 m, 4 H, H-6 and H-6'), 4.47 (d, 1 H, H-1'), 4.00 (m, 1 H, H-2), 3.87, 3.78 and 3.67 (3 m, each 1 H, H-4, H-5 and H-5'), 2.16, 2.11, 2.10, 2.04, 2.03 and 1.96 (6 s, each 3 H, 6×-OAc).

$^{13}$C NMR (CDCl$_3$) δ: 100.47 (C-1'), 85.1 (C-1), 75.99, 75.41 and 69.97 (C-4, C-5 and C-5'), 72.50 (C-3), 70.17 (C-3'), 68.42 (C-2'), 65.87 (C-4'), 61.43 and 60.26 (C-6 and C-6'), 53.66 (C-2), 21.35, 21.11, 21.11, 20.98, 20.87 and 20.75 (6×OAc).

Example 13

Similarly prepared according to example 11: compound of general formula 5, wherein R$_4$=acetyl, —NR$_5$R$_6$=—NH-trifluoroacetyl, X=β-SPh.

$^1$H NMR (CDCl$_3$) δ: 7.79 (d, 1 H, $J_{NH,2}$ 9.74 Hz, NH), 7.45 and 7.29 (2 m, 5 H, aromatic), 5.35 (dd, 1 H, $J_{3',4'}$ 3.10 Hz, $J_{4',5'}$ <1 Hz, H-4'), 5.24 (m, 1 H, H-3), 5.05 (dd, 1 H, $J_{1',2'}$ 7.59 Hz, $J_{2',3'}$ 10.44 Hz, H-2'), 4.96 (dd, 1 H, H-3'), 4.82 (d, 1 H, $J_{1,2}$ 10.35 Hz, H-L), 4.46 (d, 1 H, H-1'), 4.65 and 4.10-3.88 (m, 7 H, H-2, H-5, H-6, H-5' and H-6'), 3.76 (m, 1 H, H-4), 2.11, 2.06, 2.05, 2.04, 2.03 and 1.99 (6 s, each 3 H, 6×-OAc).

$^{13}$C NMR (CDCl$_3$) δ: 171.67, 170.63, 170.56, 170.41, 170.41, and 169.48 (6×OAc), 101.64 (C-1'), 84.44 (C-1), 76.78 (C-4), 76.25 (C-5), 71.41 (C-3), 71.09 and 70.84 (C-3' and C-5'), 69.22 (C-2'), 66.70 (C-4'), 62.06 and 60.87 (C-6 and C-6'), 52.72 (C-2).

Example 14

Similarly prepared according to example 11: compound of general formula 5, wherein $R_4$=4-chlorobenzoyl, —$NR_5R_6$=—NH-dichloroacetyl, X=β-SPh.

$^1$H NMR (CDCl$_3$) δ: 7.92-7.05 (m, 29 H, aromatic), 6.65 (d, 1 H, $J_{NH,2}$ 9.45 Hz, NH), 5.74 (s, 1 H, —CHCl$_2$), 5.65 (dd, 1 H, $J_{3',4'}$ 3.39 Hz, $J_{4',5'}$ <1 Hz, H-4'), 5.55 (dd, 1 H, $J_{1',2'}$ 7.89 Hz, $J_{2',3'}$ 10.34 Hz, H-2'), 5.53 (dd, 1 H, $J_{2,3}$ 9.01 Hz, $J_{3,4}$ 10.24 Hz, H-3), 5.32 (dd, 1 H, H-3'), 4.80 (d, 1 H, $J_{1,2}$ 10.31 Hz, H-1), 4.78 (d, 1 H, H-1'), 4.52 and 4.35 (m, 2 H, H-6), 4.01 (m, 1H, H-2), 3.91 (m, 1 H, H-4), 3.90 (m, 3 H, H-5' and H-6'), 3.67 (m, 1 H, H-5).

$^{13}$C NMR (CDCl$_3$) δ: 165.42, 165.16, 164.89, 164.74, 164.37, 164.37 and 164.25 (7×CO), 100.87 (C-1'), 86.27 (C-1), 76.98 (C-5), 75.99 (C-4), 73.99 (C-3), 71.67 (C-3'), 71.01 (C-5'), 70.12 (C-2'), 67.69 (C-4'), 66.36 (—CHCl$_2$), 62.71 and 61.05 (C-6 and C-6'), 53.42 (C-2).

Example 15

Similarly prepared according to example 11: compound of general formula 5, wherein $R_4$=benzoyl, —$NR_5R_6$=—NH-dichloroacetyl, X=β-SPh.

$^1$H NMR (CDCl$_3$) δ: 8.18-7.08 (m, 35 H, aromatic), 6.84 (d, 1 H, $J_{NH,2}$ 9.50 Hz, NH), 5.82 (s, 1 H, —CHCl$_2$), 5.77 (dd, 1 H, $J_{3',4'}$ 3.40 Hz, $J_{4',5'}$ <1 Hz, H-4'), 5.69 (dd, 1 H, $J_{1',2'}$ 7.88 Hz, $J_{2',3'}$ 10.36 Hz, H-2'), 5.53 (dd, 1 H, $J_{2,3}$ 9.05 Hz, $J_{3,4}$ 10.27 Hz, H-3), 5.42 (dd, 1 H, H-3'), 4.91 (d, 1 H, $J_{1,2}$ 10.21 Hz, H-1), 4.91 (d, 1 H, H-1'), 4.65 and 4.44 (m, 2 H, H-6), 4.14 (m, 1H, H-2), 4.05 (m, 1 H, H-4), 3.83 (m, 3 H, H-5' and H-6'), 3.73 (m, 1 H, H-5).

$^{13}$C NMR (CDCl$_3$) δ: 166.51, 165.97, 165.84, 165.67, 165.45, 165.05 and 164.39 (7×CO), 101.30 (C-1'), 86.63 (C-1), 76.86 (C-5), 75.85 (C-4), 73.91 (C-3), 71.90 (C-3'), 71.65 (C-5'), 70.11 (C-2'), 67.64 (C-4'), 66.25 (—CHCl$_2$), 62.79 and 61.28 (C-6 and C-6'), 53.72 (C-2).

Example 16

3.0 g of methyl thiolactosaminide is dissolved in 10 ml of DMF and to this solution 100 μl of triethyl amine and 6.0 ml of methyl trichloroacetate were added. The reaction mixture was stirred at rt for overnight, then concentrated to dryness, the concentrate was dissolved in methanol (10 ml), chilled and NaOMe was added until pH reached 9. This mixture was stirred for overnight, evaporated, then pyridine (20 ml) and Ac$_2$O (10 ml) were added. After 6 h the mixture was concentrated and chromatographed with hexane-acetone 6:4 to yield off-white foam (a compound of general formula 5, wherein $R_4$=acetyl, —$NR_5R_6$=—NH-trichloroacetyl, X=SMe). For characterization of the anomers an analytical sample was chromatographed, α-anomer: $^1$H NMR (CDCl$_3$) δ: 7.05 (d, 1 H, $J_{NH,2}$ 7.05 Hz, NH), 5.30 (m, 2 H, $J_{1,2}$ 5.38 Hz, H-1 and Ht-4'), 5.13 (dd, 1 H, $J_{2,3}$ 10.99 Hz, $J_{3,4}$ 8.81 Hz, H-3), 5.07 (dd, 1H, $J_{1',2'}$ 7.83 Hz, $J_{2',3'}$ 10.42 Hz, H-2'), 4.92 (dd, 1 H, $J_{3',4'}$ 3.37 Hz, H-3'), 4.49 (d, 1 H, H-1'), 4.38-4.13 (m, 2 H, H-6'), 4.26 (m, 1 H, H-2), 4.21 (m, 1 H, H-5), 4.03 (m, 2 H, H-6), 3.85 (m, 1 H, H-5'), 3.76 (m, 1 H, H-4), 2.09, 2.09, 2.07, 2.02, 2.02, 2.01 and 1.99 (7×s, each 3 H, 6×OAc and SMe). $^{13}$C NMR (CDCl$_3$) δ: 171.14, 170.28, 170.28, 170.01, 169.91, 169.03 and 161.75 (7×CO), 100.96 (C-1'), 91.67 (TCA), 83.98 (C-1), 75.89 (C-4), 70.76 (C-3'), 70.75 (C-3), 70.43 (C-5'), 68.98 (C-5), 68.91 (C-2') 66.46 (C-4'), 61.79 and 60.69 (C-6 and C-6'), 54.31 (C-2), 20.69, 20.59, 20.55, 20.47, 20.47 and 20.34 (6×OAc), 13.51 (SMe). β-anomer: $^1$H NMR. (CDCl$_3$) δ: 7.48 (d, 1 H, $J_{NH,2}$ 9.68 Hz, NH), 5.33 (m, 1 H, H-4'), 5.28 (dd, 1 H, $J_{2,3}$ 10.19 Hz, $J_{3',4'}$ 9.12 Hz, H-3), 5.02 (dd, 1 H, $J_{1',2'}$ 7.64 Hz, $J_{2',3'}$ 10.40 Hz, H-2'), 4.92 (dd, 1 H, $J_{3',4'}$ 3.27 Hz, 1 H-3'), 4.48 (m, 2 H, H-1 and H-1'), 4.15 (m, 1 H, H-2), 4.04 (m, 4 H, H-6 and H-6'), 3.86 (m, 1 H, H-5'), 3.80 (m, 1 H, H-4), 3.64 (m, 1 H, H-5), 2.15, 2.12, 2.10, 2.04, 2.03, 2.01 and 1.92 (7×s, each 3 H, 6×OAc and SMe). $^{13}$C NMR (CDCl$_3$) δ: 170.97, 170.36, 170.25, 170.06, 169.94, 169.08 and 162.23 (7×CO), 101.51 (C-1'), 92.23 (TCA), 83.03 (C-1), 76.66 and 76.66 (C-4 and C-5), 73.61 (C-3), 70.81 (C-3'), 70.55 (C-5'), 70.52 (C-2'), 66.41 (C-4') 62.09 and 60.60 (C-6 and C-6'), 53.62 (C-2), 20.85, 20.80, 20.57, 20.56, 20.52 and 20.40 (6×OAc), 11.25 (SMe).

Example 17

10 g (8.13 mmol) of the acceptor according to example 6 (a compound of general formula 6, wherein $R_1$=Bn, $R_2$=4-chlorobenzoyl, $R_3$=benzoyl, $OR_1$ in β) and 10 g (1.6 equiv.) of the donor according to example 16 (a compound of general formula 5, wherein $R_4$=acetyl, —$NR_5R_6$=trichloroacetyl, X=SMe) were dissolved in 35 ml of dry CHCl$_3$ under argon. To this solution 3.7 g of NIS and 490 mg of AgOTf were added at rt, and the stirring was continued for approx. 20 min. Triethyl amine (5 ml) was added to the slurry, diluted with CH$_2$Cl$_2$ (500 ml) and then extracted 2× with sodium thiosulphate solution (10%), the organic phase was separated, dried with MgSO$_1$, filtered, concentrated, and the syrup was chromatographed on a column of silica-gel, using gradient of CH$_2$Cl$_2$: acetone 98:2→95:5. Yield: 12.7 g, 80% (a compound of general formula 4, wherein $R_1$=Bn, $R_2$32 4-chlorobenzoyl, $R_3$=benzoyl, $R_4$=acetyl, —$NR_5R_6$=—NH-trichloroacetyl, $OR_1$ in β). MS (ESP): 1972.1 [M+Na]$^+$, 1988.1 [M+K]$^+$, 1948.2 [M-H]$^-$, 1984.0 [M+Cl]$^-$. $^{13}$C NMR (CDCl$_3$) δ: 101.2, 100.7, 100.0, 98.8 (anonmeric carbons). Mp.: 139-142° C.

Example 18

100 g (120.4 mmol) of the donor according to example 11 (a compound of general formula 5, wherein $R_4$=acetyl, —$NR_5R_6$=—NH-trichloroacetyl, X=β-SPh) and 118 g (96.2 mmol) of the acceptor according to example 6 (a compound of general formula 6, wherein $R_1$=Bn, $R_2$=4-chlorobenzoyl, $R_3$=benzoyl, $OR_1$ in β) was dissolved in 250 ml of dry CHC$_3$ under argon.

To this solution 38 g of NIS and 6 g of AgOTf were added at rt., and the stirring was continued for approx. 1 h. The slurry was diluted with CH$_2$Cl$_2$ (500 ml) and subjected to extractive work-up. The final volume of the organic phase was 1.5 L, 450 ml of 10% Na$_2$S$_2$O$_3$-solution and 150 ml of saturated NaHCO$_3$-solution was used. After the concentration, 280 g of brown syrup was isolated, which was subjected to column chromatography yielding a compound of general formula 4, wherein $R_1$=Bn, $R_2$=4-chlorobenzoyl, $R_3$=benzoyl, $R_4$=acetyl, —$NR_5R_6$=—NH-trichloroacetyl, $OR_1$ in β (physical data are identical to those of compound of example 17).

Example 19

Analogously prepared according to example 18 from donor of example 11 and acceptor of example 8: compound of general formula 4, wherein $R_1$=4-methylbenzyl, $R_2$=4-chlorobenzyl, $R_3$=benzoyl, $R_4$=acetyl, —$NR_5R_6$=—NH-trichloroacetyl, $OR_1$ in β.

White crystals from MeOH $^1$H data (CDCl$_3$): 8.0-7.25 (m, aromatic), 6.8-7.0 (m, aromatic), 6.4 (d, 1H, NH), 5.54 (m, 2H), 5.42 (dd, 1H), 5.38 (dd, 1H), 5.3 (d, 1H), 5.04 (m, 2-H), 4.92 (dd, 1H), 4.74 (d, 1H), 4.6 (m, 4H), 4.4 (m, 4H), 4.0 (m, 6H), 3.7 (m, 5-1), 3.4 (m, 2H).

$^{13}$C data (CDCl$_3$): 177.4 (NHTCA carbonyl), 170.3, 170.2, 170.1, 170.0, 169.9, 169.0 (OAc, carbonyl), 165.3, 165.1, 164.9, 164.4, 164.2, 163.5, 161.3 (OBz carbonyl), 140.2, 140.0, 139.9, 139.7, 139.4, 137.9, 133.4, 133.1, 131.2, 131.1, 130.9, 130.8, 130.7, 129.9, 129.1, 129.0, 128.9, 128.6, 128.5, 128.3, 127.9, 127.8, 127.7, 127.6, 127.5, 127.1 (aromatic carbons), 101.2, 100.7, 99.9, 98.6 (anomeric carbons), 91.7 (NHTCA CCl$_3$), 76.2, 75.4, 72.9, 72.8, 71.7, 71.6, 70.8, 70.7, 70.5, 69.5, 68.9, 66.5, 62.8, 62.1, 60.9, 60.7, 55.7, 29.5, 21.1, 20.6, 20.5, 20.4, 20.3.

Example 20

Analogously prepared according to example 18 from donor of example 11 and acceptor of example 9: compound of general formula 4, wherein $R_1$=4-chlorobenzyl, $R_2$=4-chlorobenzyl, $R_3$=benzoyl, $R_4$=acetyl, —$NR_5R_6$=—NH-trichloroacetyl, $OR_1$ in β.

$^1$H NMR (CDCl$_3$): 7.95-6.85 (m, aromatic H), 6.42 (d, 1H), 5.55 (m), 5.4 (m, 4H), 5.0 (m, 3H), 4.75 (d, 1H), 4.55 (m, 4H), 4.4 (m, 2H), 4.0 (m), 3.7 (m, 5H), 3.45 (m, 3H).

$^{13}$C NMR (CDCl$_3$): 170.32, 170.0, 169.0, 165.1, 164.4, 163.6, 161.4, 140.3, 139.9, 139.5, 134.9, 133.9, 133.4, 131.0, 130.0, 128.9, 128.6, 127.9, 127.6, 127.4, 127.1, 101.2, 100.7, 99.9, 99.2, 91.7, 76.2, 75.4, 73.0, 71.6, 70.8, 70.0, 69.6, 68.9, 68.7, 66.6, 65.4, 63.2, 62.7, 62.1, 60.8, 55.7, 53.5, 30.9.

Example 21

Glycosyl donor of example 11 (1.0 equiv.) and diol acceptor of example 2 (1.0 equiv.) was dissolved in 25 mL of CH$_2$Cl$_2$. The solution was cooled to 0° C. and NBS (1.2 equiv) was added. After 10 min, stirring 25 μL of trifluoromethanesulfonic acid was added slowly. After the reaction reached completion, it was worked up as usually. The crude product was purified by flash chromatography to give compound of general formula 4, wherein R=benzyl, $R_2$=4-chlorobenzyl, $R_3$=H, $R_4$=acetyl, —$NR_5R_6$=—NH-trichloroacetyl, $OR_1$ in β (56%).

$^{13}$C NMR (500 MHz): 170.3, 170.1, 170.0, 169.9, 169.0, 165.0, 164.9, 164.5, 164.3, 163.6, 162.0, 140.0, 139.9, 139.8, 139.7, 139.5, 137.7, 136.3, 131.2, 131.1, 131.0, 130.8, 130.7, 129.0, 128.9 (2 signals), 128.8, 128.6, 128.5, 128.3, 128.1, 128.0 (2 signals), 127.9, 127.6 (2 signals), 127.5, 127.2, 125.2, 101.1, 100.6, 99.4, 98.7, 91.6, 79.8, 75.9, 75.4, 73.2, 73.1, 72.8, 72.1, 71.9, 71.0, 70.7, 70.6, 70.5 (2 signals), 69.0, 67.4, 66.5, 62.8, 62.7, 61.7, 60.8, 55.8, 22.6, 21.3, 20.5 (2 signals), 20.4.

Example 22

10 g (5.1 mmol) of protected tetrasaccharide (example 17) was dissolved in MeOH (110 ml) and solution of NaOMe (1 M in MeOH) was added until pH 10. The solution was stirred at 40° C. for 5 h, then neutralized by addition of Amberlite IR 120H$^+$ resin, the resin was filtered off, and the filtrate was evaporated to dryness. The residue was dissolved in warm DMF (10 ml) and added dropwise to $^i$Pr$_2$O (150 ml) and the suspension was stirred for additional 3 h. The precipitate was filtered off, washed with $^i$Pr$_2$O (2×20 ml) and dried to yield 4.2 g of product (a compound of general formula 3, wherein $R_1$=Bn, —$NR_5R_6$=—NH-trichloroacetyl, $OR_1$ in β) as off-white powder (91%). MS (ESP): 900.1 [M-H]$^-$. $^{13}$C NMR (D$_2$O) δ: 105.6, 105.5, 104.2, 103.7 (anomeric carbons). Mp.: 134.5-135° C.

The same product could be prepared analogously from compound of example 21.

Example 23

Analogously prepared according to example 22 from compound of example 19: compound of general formula 3, wherein $R_1$=4-methylbenzyl, —$NR_5R_6$=—NH-1-trichloroacetyl, $OR_1$ in β.

$^1$NMR (D$_2$O): 7.25 (dd, 4H, aromatic), 4.98 (d, 1H), 4.88 (d, 1H), 4.8 (s), 4.7 (d, 1H), 4.5 (dd, 1H), 4.44 (d, 1H), 4.18 d (1H), 3.9 (m), 3.78 (m), 3.6 (m), 3.36 (s).

$^{13}$C NMR (D$_2$O): 167.7, 141.5, 136.2, 132.0, 131.7, 105.7, 105.6, 104.2, 103.7, 94.3, 84.2, 81.1, 80.9, 78.1, 77.6, 77.5, 77.4, 77.1, 75.5, 75.3, 74.5, 74.1, 73.7, 72.9, 71.3, 71.0, 63.8, 63.7, 62.9, 62.6, 60.0, 51.6, 23.0.

Example 24

Analogously prepared according to example 22 from compound of example 20: compound of general formula 3, wherein $R_1$=4-chlorobenzyl, —$NR_5R_6$=—NH-trichloroacetyl, $OR_1$ in β.

$^1$H NMR (D$_2$O): 7.2 (m, 4H, aromatic), 4.96 (d, 1H), 4.88 (d, 1H), 4.72 (d, 1H), 4.62 (d, 1H), 4.52 (m, 2H), 4.42 (m, 1H), 4.16 (d, 1H), 3.9 (m), 3.7 (m), 3.65 (m), 3.58 (m).

$^{13}$C NMR (D$_2$O): 167.7 (NHTCA carbonyl), 137.9, 136.2, 132.9, 131.3, 105.7, 105.6, 104.3, 103.8 (4× anomeric carbons), 94.3 (NHTCA CCl$_3$), 84.2, 81.4, 81.1, 80.9, 78.1, 77.6, 77.5, 77.4, 77.1, 75.5, 75.3, 74.6, 74.5, 73.7, 73.4, 72.9, 71.3, 71.0, 63.8, 63.7, 62.8, 62.6, 60.2, 60.0, 59.8.

Example 25

35 g of a compound of example 22 was dissolved in 110 ml of MeOH and 110 ml of aqueous KOH (7.5 g) solution and the mixture was stirred at rt. for 1 d. The mixture was then chilled with ice-bath, neutralized by HCl-gas and concentrated to dryness. The crude brown glass (a compound of general formula 2, wherein $R_1$=Bn, $OR_1$ in β, $^{13}$C NMR (D$_2$O) δ: 107.1, 105.7, 105.4, 103.7 (anomeric carbons)) was then acetylated with pyridine (150 ml) and acetic anhydride (150 ml) at rt. for 1 d. The solution was concentrated, the syrup was dissolved in CH$_2$Cl$_2$, the organic phase was extracted with 1M HCl-solution and then with sat. NaHCO$_3$-solution, dried with MgSO$_4$, filtered and concentrated to yield 43 g of brown foam. This was subjected to column chromatography to give a compound of general formula 4a, wherein $R_1$=Bn, $OR_1$ in β. $^{13}$C NMR (CDCl$_3$) δ: 101.2, 100.8, 100.4, 99.2 (anomeric carbons).

Example 26

Analogously prepared according to the de-N-acylation step of example 25 from compound of example 23: compound of general formula 2 wherein $R_1$=4-methylbenzyl, $OR_1$ in β.

$^1$H NMR (D$_2$O): 7.3 (dd, 4H, aromatic), 4.9 (d, 1H), 4.72 (dd, 1H), 4.5 (m), 4.18 (d, 1H), 3.95 (m), 3.8-3.55 (m), 3.34 (dd).

$^{13}$C NMR (D$_2$O): 184.1, 141.4, 136.6, 136.1, 131.9, 131.6, 131.4, 105.7, 105.3, 105.2, 100.0, 84.8, 81.0, 80.9, 78.0, 77.7, 77.5, 77.4, 77.1, 75.9, 75.5, 75.2, 74.4, 74.0, 73.6, 73.2, 72.7, 72.4, 71.2, 70.9, 63.7, 63.6, 62.5, 58.9, 25.9.

Example 27

Analogously prepared according to the de-N-acylation step of example 25 from compound of example 24: compound of general formula 2 wherein R$_1$=4-chlorobenzyl, OR$_1$ in β.
$^1$H NMR (D$_2$O): 7.4 (s, 4H, aromatic), 4.9 (m, 2H), 4.75 (m), 4.52 (dd, 1H), 4.46 (dd, 1H), 4.18 (d, 1H), 3.96 (m), 3.86 (m), 3.7 (m), 3.62 (m).
$^{13}$C NMR (D$_2$O): 184.1, 137.9, 136.2, 132.9, 132.6, 131.3, 105.7, 105.2, 104.0, 103.8, 84.6, 80.9, 80.7, 78.1, 77.6, 77.4, 77.1, 75.5, 75.2, 74.4, 73.6, 73.4, 72.7, 71.2, 70.9, 63.8, 63.6, 62.8, 62.4, 58.6, 51.6, 25.9.

Example 28

140 g (107.5 mmol) of the peracetylated tetrasaccharide (example 25) was dissolved in 1.5 L of MeO-1H, NaOMe-solution (1M) was added until pH 10, and the mixture was stirred at 50° C. overnight. The product crystallized from the reaction mixture. The mixture was allowed to cool to rt., then it was chilled, filtered, the filtrate was washed with cold EtOH, then dried to yield 69 g of white powder (a compound of general formula 1, wherein R$_1$=Bn, OR$_1$ in β; 80%). $^{13}$C NMR (D$_2$O) δ: 105.6, 105.5, 105.4, 103.6 (anomeric carbons). Mp.: 284-286° C.

Example 29

150 g of purified amine (compound of general formula 2, R$_1$=benzyl, OR$_1$ in β) were added to a mixture of water (150 mL) and MeOH (200 mL) at room temperature. Acetic anhydride (20 mL) was added in one portion. After 1 h stirring extra 10 mL of acetic anhydride added and the mixture was stirred at r.t. After 1 h stirring extra 10 mL of acetic anhydride added and the mixture was stirred for additional 2 h at r.t. At the end the mixture was a crystalline mass. MeOH (250 mL) was added and the mixture was put to fridge for overnight. The solid was filtered, the cake was washed with cold MeOH (200 mL) to yield 260 g of light brown solid. Drying of this solid at 50° C. at atmospheric pressure (3 days) yielded 118 g of product (compound of general formula 1, R$_1$=Bn, OR$_1$ in β). Recrystallization of 80 g in MeOH/water yielded 72.6 g product with 99.7% purity according to HPLC.

Example 30

Analogously prepared according to example 29 from compound of example 26: compound of general formula 1, R$_1$=4-methylbenzyl, OR$_1$ in β.
$^1$H NMR (D$_2$O): 7.3 (dd, 4H), 4.88 (d, 1H), 4.7 (m), 4.54 (d, 1H), 4.48 (d, 1H), 4.42 (d, 1H), 4.34 (d), 4.0-3.5 (m), 3.34 (dd, 1H).
$^{13}$C NMR (D$_2$O): 184.2, 177.6, 173.7, 141.5, 136.1, 131.9, 131.4, 105.6, 105.5, 105.4, 103.6, 93.2, 84.7, 81.5, 81.0, 80.8, 78.0, 77.6, 77.4, 77.1, 75.5, 75.2, 74.8, 74.0, 73.6, 72.9, 63.7, 62.8, 58.9, 56.4, 25.9, 22.9.

Example 31

Analogously prepared according to example 29 from compound of example 27: compound of general formula 1, R$_1$=4-chlorobenzyl, OR$_1$ in β.
$^1$H NMR (D$_2$O): 7.4 (s, 4H), 4.9 (d, 1H), 4.72 (m), 4.52 (d, 1H), 4.8 (d, 1H), 4.42 (d, 1H), 4.16 (d, 1H), 4.0-3.52 (m).
$^{13}$C NMR (D$_2$O): 138.9, 177.6, 138.3, 137.9, 136.2, 131.3, 105.6, 105.5, 105.4, 103.7, 93.2, 86.1, 84.7, 81.5, 81.0, 80.8, 78.0, 77.5, 77.4, 77.2, 77.1, 75.5, 75.2, 74.9, 63.7, 58.9, 57.8, 56.4, 24.8.

Example 32

40 g (50.1 mmol) of the benzyl glycoside (example 28 or 29) were dissolved in 200 ml of water, 1.6 g of Pd—C and 400 μl of acetic acid was added, and the mixture was stirred at rt. under H$_2$-atmosphere (approx. 40 bars) for 2 days. The catalyst was filtered off, the cake was washed with water, and the filtrate was added dropwise to 1.6 l of acetone, then chilled, filtered and the collected solid was dried under vacuum to yield 31.5 g of white powder of LNnT (44.5 mmol, 89%).

Example 33

Benzyl glycoside (example 28 or 29, 100 g) was dissolved in 300 ml of water, 2 ml of acetic acid and 30 ml of MeOH was added, then 10 g of Pd—C (5%). The mixture was hydrogenated at r.t. under 5 bar of hydrogen for 2 days. Activated carbon (5 g) was added to the mixture, the catalyst and carbon were filtered off, the filtrate was diluted with water (200 ml), the aqueous solution was heated to 50° C. The crystallization was performed as above by addition of EtOH (4 L). 65 g of white solid of LNnT was isolated.

Example 34

50 g of the benzyl glycoside (example 28 or 29) were dissolved in 110 mL of water and the solution was diluted with MeOH (120 mL). Pd—C (2 g, 10% Pd) catalyst was added, and the mixture was hydrogenated at 60° C. under H$_2$ atmosphere (5 bars). After 7 h the catalyst was filtered off, the cake was washed with approx. 20 mL of water:MeOH mixture (1:1).
Crystallization: the solution obtained above was warmed (50-55° C.) to which hot MeOH (600 mL) was added in 3-5 portions under gradual chilling to 40° C. Crystallization started immediately. After addition of the methanol the crystalline mixture was slowly (3 h) cooled to r.t., then put to the fridge for overnight. Filtered on glass filter, the solid was washed with cold MeOH. and dried at 60° C. in a vacuum drying oven for 2 days to yield 37.4 g of white solid. HPLC purity: 100%, mp.: 226-230° C. $^{13}$C-NMR (600 MHz, D$_2$O: CD$_3$OD=3:2) δ: Glc (α) C-1 93.2 C-2 72.5 C-3 72.7 C-4 79.5 C-5 71.3 C-6 61.2, Glc (β) C-1 97.2 C-2 75.2 C-3 75.7 C-4 79.5 C-5 76.1 C-6 61.3, Gal C-1 104.3 C-2 71.4 C-3 83.1 C-4 69.7 C-5* 76.2 C-6 62.3, GlcNAc C-1 104.1 C-2 56.4 C-3 73.4 C-4 79.2 C-5 75.8 C-6 61.0 NCOCH$_3$ 23.3 174.8, Gal C-1 104.2 C-2 72.3 C-3 73.9 C-4 69.9 C-5* 76.6 C-6 62.3 (* interchangeable assignments).

The invention claimed is:
1. A polymorph of Galpβ1-4GlcNAcpβ1-3Galpβ1-4Glc (LNnT), characterized in that it displays X-ray powder diffraction reflections, based on a measurement using CuKα radiation, at 20.32±0.20, 19.10±0.20, 7.98±0.20, 21.03±0.20, 20.95±0.20 and 5.66±0.20 2Θ angles.
2. The polymorph of Galpβ1-4GlcNAcpβ1-3Galpβ1-4Glc according to claim 1, which displays a melting point between 226-230° C.
3. A pharmaceutical composition comprising the polymorph of Galpβ1-4GlcNAcpβ1-3Galpβ1-4Glc as defined in claim 1.
4. A nutritional composition comprising the polymorph of Galpβ1-4GlcNAcpβ1-3Galpβ1-4Glc as defined in claim 1.

5. A compound of general formula 3

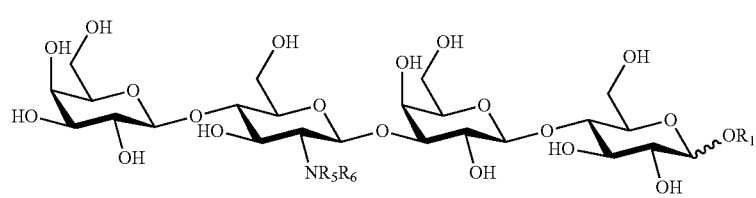

general formula 3 wherein $R_1$ is selected from optionally substituted benzyl, optionally substituted benzhydryl, optionally substituted trityl and optionally substituted naphthylmethyl, and —$NR_5R_6$ is —NH-haloacyl.

6. The compound according to claim 5, wherein $R_1$ is selected from benzyl, 4-methylbenzyl and 4-chlorobenzyl.

7. The compound according to claim 6, wherein —$NR_5R_6$ is —NH-trichloroacetyl.

8. A compound of general formula 4

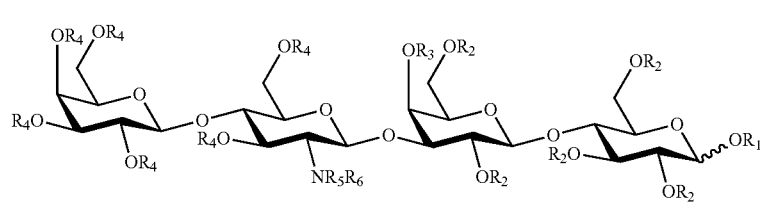

general formula 4 wherein $R_1$ is selected from optionally substituted benzyl, optionally substituted benzhydryl, optionally substituted trityl and optionally substituted naphthylmethyl, and each of $R_2$ and $R_4$ are independently optionally substituted acyl, $R_3$ is selected from optionally substituted acyl and H, and —$NR_5R_6$ is —NH-haloacyl.

9. The compound according to claim 8, wherein $R_1$ is selected from benzyl, 4-methylbenzyl and 4-chlorobenzyl, $R_2$ is benzoyl optionally substituted by chloro, $R_3$ is optionally substituted benzoyl and $R_4$ is acetyl.

10. The compound according to claim 9, wherein $R_3$ is benzoyl, and —$NR_5R_6$ is —NH-trichloroacetyl.

11. A compound of general formula 5' general formula 5'

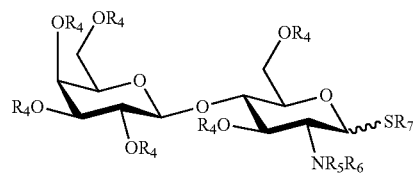

wherein $R_4$ is optionally substituted acyl, —$NR_5R_6$ is —NH-haloacyl, and $R_7$ is optionally substituted phenyl.

12. The compound according to claim 11 wherein $R_4$ is acetyl, —$NR_5R_6$ is —NH-trichloroacetyl or —NH-trifluoroacetyl, and $R_7$ is phenyl.

13. A compound of general formula 6' general formula 6'

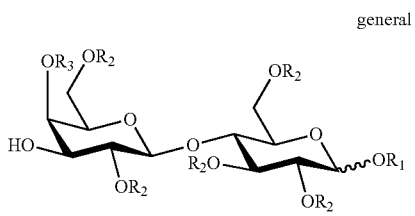

wherein $R_1$ is selected from optionally substituted benzyl, optionally substituted benzhydryl, optionally substituted trityl and optionally substituted naphthylmethyl, $R_2$ is optionally substituted benzoyl, and $R_3$ is selected from optionally substituted acyl and H.

14. The compound according to claim 13, wherein $R_2$ is benzoyl or 4-chlorobenzoyl, and $R_3$ means benzoyl or H.

* * * * *